US009095598B2

(12) United States Patent
Radominska-Pandya et al.

(10) Patent No.: US 9,095,598 B2
(45) Date of Patent: *Aug. 4, 2015

(54) STILBENOID DERIVATIVES AND THEIR USES

(75) Inventors: Anna Radominska-Pandya, Little Rock, AR (US); Paul L. Prather, Little Rock, AR (US); Luis Fabricio Medina-Bolivar, Memphis, TN (US); Philip R. Mayeux, Little Rock, AR (US)

(73) Assignees: The Board of Trustees of the University of Arkansas, Little Rock, AR (US); Arkansas State University—Jonesboro, Jonesboro, AR (US)

( * ) Notice: Subject to any disclaimer, the term of this patent is extended or adjusted under 35 U.S.C. 154(b) by 73 days.

This patent is subject to a terminal disclaimer.

(21) Appl. No.: 13/339,163

(22) Filed: Dec. 28, 2011

(65) Prior Publication Data
US 2012/0165281 A1 Jun. 28, 2012

Related U.S. Application Data

(60) Provisional application No. 61/427,614, filed on Dec. 28, 2010.

(51) Int. Cl.
*A61K 31/7034* (2006.01)
*C07H 15/207* (2006.01)

(52) U.S. Cl.
CPC .................................. *A61K 31/7034* (2013.01)

(58) Field of Classification Search
USPC .............................. 514/35; 536/18.2; 435/375
See application file for complete search history.

(56) References Cited

U.S. PATENT DOCUMENTS

| | | | |
|---|---|---|---|
| 4,241,046 A | 12/1980 | Papahadjopoulos et al. | |
| 4,394,448 A | 7/1983 | Szoka, Jr. et al. | |
| 4,529,561 A | 7/1985 | Hunt et al. | |
| 4,755,388 A | 7/1988 | Heath et al. | |
| 4,828,837 A | 5/1989 | Uster et al. | |
| 4,925,661 A | 5/1990 | Huang | |
| 4,954,345 A | 9/1990 | Muller | |
| 4,957,735 A | 9/1990 | Huang | |
| 5,043,164 A | 8/1991 | Huang et al. | |
| 5,064,655 A | 11/1991 | Uster et al. | |
| 5,077,211 A | 12/1991 | Yarosh | |
| 5,264,618 A | 11/1993 | Felgner et al. | |
| 6,136,839 A | 10/2000 | Isakson et al. | |
| 6,448,450 B1 * | 9/2002 | Nag et al. | 568/646 |
| 6,552,085 B2 * | 4/2003 | Inman et al. | 514/576 |
| 6,710,037 B2 | 3/2004 | Wang et al. | |
| 7,384,920 B2 * | 6/2008 | Li et al. | 514/23 |
| 8,410,064 B2 | 4/2013 | Radominska-Pandya et al. | |
| 8,883,218 B2 | 11/2014 | Radominska-Pandya et al. | |
| 2002/0198167 A1 | 12/2002 | Czernik et al. | |
| 2003/0215462 A1 | 11/2003 | Wacher et al. | |
| 2005/0074745 A1 | 4/2005 | Clayton et al. | |
| 2006/0153808 A1 | 7/2006 | Cristofanilli et al. | |
| 2006/0275371 A1 | 12/2006 | Dai et al. | |
| 2007/0259894 A1 | 11/2007 | Kassahun | |
| 2010/0226856 A1 | 9/2010 | Vitaliano et al. | |
| 2010/0273203 A1 | 10/2010 | Miller et al. | |
| 2011/0046081 A1 | 2/2011 | Radominska-Pandya et al. | |
| 2011/0236495 A1 | 9/2011 | Radominska-Pandya et al. | |
| 2012/0165280 A1 | 6/2012 | Mayeux et al. | |
| 2012/0184536 A1 | 7/2012 | Radominska-Pandya | |

FOREIGN PATENT DOCUMENTS

| | | | | |
|---|---|---|---|---|
| WO | WO 99/59561 | * | 11/1999 | ............. A61K 31/00 |
| WO | 2011026112 A1 | | 8/2010 | |
| WO | 2011017456 A2 | | 2/2011 | |

OTHER PUBLICATIONS

Merck Manual, 1992, 16th Ed., pp. 446-47, 522-23, 1274.*
Liu et al, Biochemical Journal, 2000, 346, pat. 2, pp. 835-840.*
Olas et al, Cell Biology and Toxicology, 2008, 24, 331-40.*
Liu et al, Biochemical Journal, 2000, 346, part. 2, pp. 835-840.*
Au, Pharmacogenics of 4-hydroxycoumarin anticoagulants. Drug Metab. Rev. 40, 355-375.
Banfield et al., Phenylbutazone-Warfarin Interaction in Man: Further Stereochemical and Metabolic Considerations. Br. J. Clin. Pharmaca. (1983), 16, 669-675.
Barua, et al., Chemical synthesis and growth promoting activity of all-trans-retinyl beta-D-glucuronide. Biochem. J. 1987, 244, pp. 231-234.
Blaner, et al., Retinol and retinoic acid metabolism: The Retinoids. Biology, Chemistry, and Medicine (Spom MB. Roberts AB and Goodman DS eds.) (1994), pp. 229-255. Raven Press, New York.
Bristol-Myers Medication Guide for Coumadin Tablets (Warfarin Sodium Tablets, USP) distributed by Bristol-Myers Squibb, Jan. 2009, 6 pages.
Brotchie, J., et al., CBI cannabinoid receptor signaling in Parkinson's disease. Current Opinion in Pharmacology. (2003), 3:54-61 (abstract only).
Court et al., Evaluation of 3'-azido-3'-deoxylhymidine, morphine, and codeine as probe substrates for UDP-glucuronosyltransferase 2B7 (UGT2B7) in human liver microsomes: specificity and influence of the UGT2B7*2 polymorphism. Drug Metab Dispos., (2003), 31(9):1125-1133.
Chan, et al., Disposition of Warfarin Enantiomers and Metabolites in Patients during Multiple Dosing with rac-warfarin. Br. J. Clin. Phamnac. (1994) 37: 563-567.
Cooper et al., Genome-wide Scan for Common Genetic Variants with a Large Influence on Warfarin maintenance dose. Blood, Aug. 15, 2008, vol. 112, No. 4, p. 1022.
Dettmer et al., Mass-Spectroscopy Based Metabolomics. Mass. Spectrom. Rev. (2007), 26(1):51-78.
Elbe, et al., A Comparison of the Isomers of Warfarin. Biochem. Pharmacol., 15:1003-1006.
Gailiegue, S., et al., Expression of central and peripheral cannabinoid receptors in human immune tissues and leukocyte subpopulations. European Journal of Biochemistry. (1995), 232:54-61.
Gallup, J., et al., Effects of retinoid betaglucuronides and N-retinoyl amities on the differentiation of HL-60 cells in vitro. Proc. Soc. Exp. Thal., (1987), 186:269-274 (abstract only).

(Continued)

*Primary Examiner* — Ganapathy Krishnan
(74) *Attorney, Agent, or Firm* — Polsinelli PC

(57) ABSTRACT

The present invention generally provides stilbenoid derivatives and methods for using stilbenoid derivatives to modulate the activity of cannabinoid receptors or scavenge reactive nitrogen species.

12 Claims, 14 Drawing Sheets

(56) References Cited

OTHER PUBLICATIONS

Gebaurer, M., Synthesis and structure-activity relationships if novel Warfarin Derivatives. Bioorg. Med. Chem., 15, 2414-2420.

Grancharov, et al., Natural and synthetic inhibitors of UDP-glucuronosyltransferase. Pharmacology & Therapeutics. (2001), 89(2):171-186.

Haining, et al., Allelic Variants of Human Cytochrome P450 2C9: Baculovirus-mediated expression, purification, structural characterization, substrate stereoselectivity and prochiral selectivity of the wild-type and 1359Lmutant forms. Arch. Biochem. Biophys. 333, 447-458.

Hirsch, et al., Oral Anticoagulants: Mechanism of Action, Clinical Effectiveness, and Optimal Therapeutic Range. Chest 2001; 119: 8S-21S.

Holbrook, et al., Systematic Overview of Warfarin and Its Food Interactions. Arch. Intern Med., May 23, 2005, vol. 165.

Howlett, A., Pharmacology of cannabinoid receptors. Annual Review of Pharmacology and Toxicology, (1995), 35:607-634.

Hyland et al., in vitro and in vivo glucuronidation of midazolam in humans. Br J Clin Pharmacol. Apr. 2009, 67 (4):445-54.

International Search Report and Written Opinion for PCT Application No. PCT/US10/47340, Oct. 26, 2010, 7 pages.

Iversen L., et al., Cannabinoids: a real prospect for pain relief. Current Opinion in Pharmacology, (2002), 2:50-55.

Janick-Buckner, D., et al., Induction of HL-60 cell differentiation by water-soluble and nitrogen-containing conjugates of retinoic acid and retinol. Faseb J., (1991), 5:320-325.

Jansing, et al., Phase II Metabolism of Warfarin in Primary Culture of Adult Rat Hepatocytes. Mol. Pharmacol., 41, 209-215.

Kaminsky, et al., Human P450 metabolism of Warfarin. Pharmcol. Ther. 67-74.

Kaminsky, et al., Correlation of human cytochrome P4502C substrate specificities with primary structure: Warfarin as probe, Mol. Pharmacol. 43, 234-239.

Klein, T., et al., The cannabinoid system and immune modulation. J. of Leukocyte Biology, (2003), 74:486-496.

Kurkeia M., et al., Expression and characterization of recombinant human UDPglucuronosyltransferases (UGTs). UGT I A9 is more resistant to detergent inhibition than other UGTs and was purified as an active dimeric enzyme, J. Biol. Chem., (2003), 278:3536-3544.

Kuuranne T., et al., Glucuronidation of anabolic androgenic steroids by recombinant human LDP glucuronosyltransferases. Drug Metab. Dispos., (2003), 31:1117-1124.

Lee et al., .Metabolism of Vitamin K and Vitamin K 2,3-epoxide via interaction with common disulfide. Biochemistry 23, 2246-2252.

Lesko, L., The Critical Path of Warfarin Dosing: Finding a Optimal Dosing Strategy Using Pharmacogenetics. Clin. Pharmacol. Ther., (2008), 84, 301-303.

Limdi, et al., Kidney Function Influences Warfarin Responsiveness and Hemorrhagic Complications, J. Am. Soc. Nephrol., (2009), 20: 912-921.

Little, J., et al., Glucuronidation of oxidized fatty acids and prostaglandins B1 and E2 by human hepatic and recombinant LIDP-alucuronosyltransferases. J. Lipid Res., (2004), 45:1694-1703.

Matsuda, L., et al., Structure of a cannabinoid receptor and functional expression of the cloned cDNA. Nature, (1990), 346:561-564.

Miller, et al., Assessing Cytochrome P450 and UDP-Glucuronosyltransferase Contributions to Warfarin Metabolism in Humans, Chem. Res. Toxicol., Jul. 2009, (22)7: 1239.

Miller et al., Identification of Hydroxywarfarin Binding Site in Human UDP Glucuronosyltransferase 1A10: Phenalyalanine90 Is Crucial for Glucuronidation of 6- and 7-Hydroxywarfarin, Drug Metabolism and Disposition, (2008), vol. 36. No. 11. 2211.

Munro, S., et al., Molecular characterization of a peripheral receptor for cannabinoids. Nature, (1993), 365:61-65.

Ngui, et al., In Vitro Stimulation of Warfarin Metabolism by Quinidine: Increases in the Formation of 4'- and 10-hydroxywarfarin, Drug Metabolism and Disposition, (2001), vol. 29, No. 6.

O'Reilly, et al., Interaction of the Anticoagulant Drug Warfarin and Its Metabolites with Human Plasma Albumin, J. Clin. Investigation, (1969), vol. 48.

Racz, et al., A critical role for the cannabinoid CB 1 receptors in alcohol dependence and stress-stimulated ethanol drinking. J. of Neuroscience, (2003), 23;2453-2458.

Radominska, et al., Photoaffinity labeling for evaluation of uridinyl analogs as specific inhibitors of rat liver rnicrosomal UDP-glucuronosyltransferases. Biochimica et Biophysica Acta (BBA)—Protein Structure and Molecular Enzymology, (1994), 1205(2):336-345.

Radominska-Pyrek, A., et al., Glucuronidation of 6 alpha-hydroxy bile acids by human liver microsomes. J Clin. invest, (1987), 80:234-241.

Rettie, et al., Hydroxylation of Warfarin by Human cDNA-expressed cytochrome P-450: A role for P-4502C9 in the etiology of (S)-warfarin drug interactions. Chem. Res. Toxicol., 5, 54-59.

Ritter, et al., Roles of Gluconuronidation and UDP-glucuronosyl transferases in xenobiotic bioactivation reactions, Chem.-Biol. Interact, 129, 171-193.

Ravinet, T., et al., Anti-obesity effect of SR 141716, a CB1 receptor antagonist; in diet induced obese mice. American Journal of Physiological Regulatory Integrative Comparative Physiology, (2002), 284; 345-353.

Wadelius, et al., Association of Warfarin Dose with Genes Involved in its Action or Metabolism, Human Genet., (2007) 121:23-3.

Wang, et al., Identification of the Human Enzymes Involved in the Oxidative Metabolism of Dasatinib: An Effective Approach for Determining Metabolite Formation in Kinetics, Drug Metabolism and Disposition, (2008), vol. 36, No. 9.

Weinkers, et al., Formation of R-(8)-hydroxywarfarin in human liver microsomes: A New Metabolic Marker for the (S)-mephenytoin hydroxylase, P4502C18. Drug Metab. Dispos., 24, 610-614.

Wen Z., et al., UDPglucuronosyltransferase 1A1 is the principal enzyme responsible for etoposide glucuronidation in human liver and intestinal microsomes: structural characterization of phenolic and alcoholic Oucuronides of etoposide and estimation of enzyme kinetics. Drug Metab. Dispos., (2007), 35:371-380.

Wittwer, E., et al., Role of morphine's metabolites in analgesia: concepts and controversies. American Association of Pharmaceutical Scientists, (2006), 8:E348-352.

Battaglia, E. et al., "Characterization of a new class of inhibitors of the recombinant human liver UDP-glucuronosyltransferase, UGT1*6," Biochim. Biophys. Acta., Jan. 18, 1995, pp. 9-14, vol. 1243, No. 1.

Gall, W., et al., "Differential glucuronidation of bile acids, androgens and estrogens by human UGT1A3 and 2B7," J Steroid Biochem. And Mol. Biol., 1999, pp. 101-108, vol. 70.

Gustafson, R. et al., "Validated method for the simultaneous determination of Δ9-tetrahydrocannibol (THC), 11hydroxy-THC and 11-nor-9-carboxy-THC in human plasma using solid phase extraction and gas chromatographymass spectrometry with positive chemical ionization," Journal of Chromatography B, 2003, pp. 145-154, vol. 798.

International Search Report and Written Opinion mailed Jun. 6, 2012 for related International Patent Application No. PCT/US2012/026578; 10 pages.

Jones, D. et al., "Warfarin and UDP-glucuronosyltransferases: writing a new chapter of metabolism," Drug Metabolism Reviews, 2010, pp. 55-61, vol. 42, No. 1.

Kuzmic, P., "Program Dynafit for the Analysis of Enzyme Kinetic Data: Application to HIV Protease," Analytical Biochem., 1996, pp. 260-273, vol. 237, Article No. 0238.

Larkin, M. et al., "Clustal W and Clustal X version 2.0," Bioinformatics, 2007, pp. 2947-2948, vol. 23, No. 21.

Little, J. et al., "Characterization of Human Liver Microsomal UDP-Glycosyltransferases using Photoaffinity Analogs," J. Pharmacol. Exp. Ther., 1995, pp. 1551-1559, vol. 273, No. 3.

Locatelli, I. et al., "Determination of warfarin enantiomers and hydroxylated metabolites in human blood plasma by liquid chromatography with achiral and chiral separation," Journal of Chromatography B, 2005, pp. 191-198, vol. 818.

(56) References Cited

OTHER PUBLICATIONS

Lyle, M. et al., "Synthesis and Characterization of Glucuronides of Cannabinol, Cannabidiol, Δ9-Tetrahydrocannabinol and Δ8-Tetrahydrocannabinol," Biomedical Mass Spectrometry, 1977, pp. 190-196, vol. 4, No. 3.

Miley, M., et al., "Crystal Structure of the Cofactor-Binding Domain of the Human Phase II Drug-Metabolism Enzyme UDP-Glucuronosyltransferase 2B7," J. Mol. Biol., Jun. 1, 2007, pp. 498-511, vol. 369, No. 2.

Naef, M. et al., "The analgesic effect of oral delta-9-tetrahydrocannabinol (THC), morphine, and a THC-morphine combination in healthy subjects under experimental pain conditions," Pain, 2003, pp. 79-88, vol. 105.

Newton, D. et al., "Evaluation of Specificities in the In Vitro Metabolism of Therapeutic Agents by Human Liver Microsomes," Drug Metabolism and Disposition, 1995, pp. 154-158, vol. 23, No. 1.

Offen, W. et al., "Structure of a flavonoid glucosyltransferase reveals the basis for plant natural product modification," Embo. J., 2006, pp. 1396-1405, vol. 25, vol. 6.

Office Action dated Jun. 21, 2012 for related U.S. Appl. No. 12/862,501; 10 pages.

Paul, P. et al., "Synthesis and Characterization of a New Class of Inhibitors of Membrane-associated UDP-Glycosyltransferases," J. Biol. Chem., Jun. 15, 1993, pp. 12933-12938, vol. 268, No. 17.

Panyam, J. et al., "Biodegradable nanaparticles for drug and gene delivery to cells and tissue," Advanced Drug Delivery Reviews, 2003, pp. 329-347, vol. 55.

Radominska, A. et al., "Characterization of UDP-glucuronic acid transport in rat liver microsomal vesicles with photoaffinity analogs," Biochim. Biophys. Acta, Oct. 12, 1994, pp. 63-70, vol. 1195, No. 1.

Radominska-Pandya, A. et al., "Structural and Functional Studies of UDP-Glucuronosyl Transferases," Drug Metab. Rev., 1999, pp. 817-899, vol. 31, No. 4.

Reynolds, K. et al., "Individualizing warfarin therapy," Personalized Medicine, 2007, pp. 11-31, vol. 4, No. 1.

Ali, A. et al., "Comparative Protein Modelling by Satisfaction of Spatial Restraints," J. Mol. Biol., Dec. 5, 1993, pp. 779-815, vol. 234, No. 3.

Steward, D. et al., "Genetic association between sensitivity to warfarin and expression of CYP2C9*3," Pharmacogenetics, Oct. 1997, pp. 361-367, vol. 7, No. 5 (Abstract Only, 1 page).

Takahashi, H. et al., "Comparisons between in-vitro and in-vivo metabolism of (S)-warfarin: catalytic activities of cDNA-expressed CYP2C9, its Leu359 variant and their mixture versus unbound clearance in patients with the corresponding CYP2C9 genotypes," Pharmacogenetics, Oct. 1998, pp. 365-373, vol. 8, No. 5 (Abstract Only, 2 pages).

Weinmann, W. et al., "Simultaneous determination of THC-COOH and THC-COOH-glucuronide in urine samples by LC/MS/MS," Forensic Science International, 2000, pp. 381-387, vol. 113.

Xiong, Y., et al., Phenylalanine 90 and 93 are localized within the phenol binding site of human UDPglucuronosyltransferase 1A10 as determined by photoaffinity labeling, mass spectrometry, and site-directed mutagenesis. Biochemist, (2006), 45:2322-2332.

Yamamoto, I., et al., The pharmacological activity of cannabinol and its major metabolite, 11-hydroxycannabinol. Chemical and Pharmaceutical Bulletin, (1987), 35:2144-2147.

Zielinska, et al., Glucuronidation of Monohydroxylated Warfarin Metabolites by Human Liver Microsomes and Human Recombinant UDP-Glucuronoxyltransferases, (2008), pp. 39-148, vol. 324, No. 1.

Zhang, et al., Human Cytochrome P450 1A1 and 1A2: R-warfarin as a probe, Drug Metab. Dispos., 23, 1339-1345.

Wu et al., "Evidence for the Role of Reactive Nitrogen Species in Polymicrobial Sepsis-Induced Renal Peritubular Capillary Dysfunction and Tubular Injury", J. Am. Soc. Nephrol., 2007, Chapter 18.

Bianco, A. et al., "Applications of carbon nanotubes in drug delivery," Current Opinion in Chemical Biology, 2005, pp. 674-679, vol. 9.

Lacerda, L. et al., "Cell-penetrating CNTs for delivery of therapeutics," Nanotoday, Dec. 2007, pp. 38-43, vol. 2, No. 6.

Notice of Allowance dated Dec. 3, 2012 for related U.S. Appl. No. 12/862,501; 5 pages.

Office Action dated Nov. 20, 2012 for related U.S. Appl. No. 13/073,270; 12 pages.

Prato, M. et al., "Functionalized Carbon Nanotubes in Drug Design and Discovery," Accounts of Chemical Research, Jan. 2008, pp. 60-68, vol. 41, No. 1.

Moran, J. et al., "LC-Ms/ms Characterization of Warfarin Metabolites Excreted in Human Urine," Oct. 3, 2008, Abstracts, 64th Southwest Regional Meeting of the ACS, 1 page.

NYU Medical Center, Patient & Family Education, "Managing Your Warfarin (Coumadin®) Therapy A Patient's Guide," Mar. 2002, 15 pages.

Office Action dated Aug. 1, 2012 for related U.S. Appl. No. 12/766,635; 12 pages.

Smith, S. et al., "Plasma pharmacokinetics of warfarin enantiomers in cats," J. Vet. Pharmacol. Ther., Dec. 2000, pp. 329-337, vol. 23, No. 6 (abstract only; 1 page).

Barbier et al., "3'-azido-3'-deoxythimidine (AZT) is glucoronidated by human UDP-glucoronosyltransferase 2B7 (UGT2B7)", Drug Met. Disp., 2000, pp. 497-502, vol. 28, No. 5.

Egan et al., "Rapid and sensitive determination of coumarin and 7-hydroxycoumarin and its glucuronide conjugate in urine and plasma by high-performance liquid chromatography", Journal of Chromatography, 1992, pp. 137-143, vol. 582.

Langenberg et al., "The histopathology of septic acute kidney injury: a systematic review", Critical Care, 2008, pp. 1-7, vol. 12, No. 2.

Office Action from related U.S. Appl. No. 13/406,177, dated Mar. 13, 2013; 14 pgs.

Office Action from related U.S. Appl. No. 12/766,635, dated Apr. 17, 2013; 16 pgs.

Office Action from related U.S. Appl. No. 13/073,270, dated May 30, 2013; 11 pgs.

Office Action from related U.S. Appl. No. 12/766,635, dated Oct. 28, 2013; 17 pgs.

Office Action from related U.S. Appl. No. 13/406,177, dated Nov. 21, 2013; 10 pgs.

Office Action from related U.S. Appl. No. 13/073,270, dated Dec. 17, 2013; 11 pgs.

Office Action from related U.S. Appl. No. 13/339,150, dated Jan. 30, 2014; 18 pgs.

Office Action from related U.S. Appl. No. 13/339,150, dated Aug. 6, 2014; 15 pgs.

Kolgazi et al., "Resveratrol Reduces Renal and Lung Injury Caused by Sepsis in Rats", Journal of Surgical Research, 2006, pp. 315-321, vol. 134, No. 2.

Office Action from related U.S. Appl. No. 13/339,150, dated Dec. 19, 2014; 22 pgs.

Notice of Allowance from related U.S. Appl. No. 13/073,270, dated Apr. 21, 2014; 7 pgs.

Notice of Allowability from related U.S. Appl. No. 13/073,270, dated Oct. 10, 2014; 7 pgs.

Holcapek et al., "High-performance liquid chromatography—tandem mass spectrometry in the identification and determination of phase I and phase Ii drug metabolites", Anal Bioanal Chem, 2008, pp. 59-78, vol. 391.

Office Action from related U.S. Appl. No. 12/766,635, dated Jan. 29, 2015; 19 pgs.

* cited by examiner

STILBENOID DERIVATIVES AND THEIR USES

CROSS REFERENCE TO RELATED APPLICATIONS

This application claims the priority of U.S. provisional application No. 61/427,614, filed Dec. 28, 2010, which is hereby incorporated by reference in its entirety.

GOVERNMENTAL RIGHTS

This invention was made with government support under DK601109, DK075991, GM075893, and NSO58430 awarded by the National Institutes of Health and with support under EPS-0701890 awarded by the National Science Foundation. The government has certain rights in the invention.

FIELD OF THE INVENTION

The present invention generally relates to stilbenoid derivatives. In particular, it relates to the use of stilbenoid derivatives to modulate the activity of cannabinoid receptors or scavenge reactive nitrogen species.

BACKGROUND OF THE INVENTION

There is an increasing demand for effective natural, non-toxic therapeutic agents to treat or prevent diseases, improve human health and promote longevity. Trans-resveratrol (tRes), a naturally occurring plant stilbenoid has been the focus of great attention because it is an efficacious antioxidant and anti-inflammatory agent with numerous potential therapeutic applications. Few natural compounds with such a broad spectrum of activities resulting from simultaneous interactions with multiple molecular targets and showing such impressive health benefits have been identified. Although initial pre-clinical studies are encouraging, the oral bioavailability of native, free tRes following rapid absorption is poor due to swift conjugation to glucuronides and sulfates. Additionally, tRes is a strong inhibitor of several important enzymes of the cytochrome P450 (CYP) system. The rapid metabolism of tRes generally is viewed as the critical barrier to clinical development of this potentially valuable therapeutic agent. Increasing the dose of tRes, however, may not be a good option to overcoming its limited bioavailability because this could lead to unpredictable drug interactions via alterations in CYP metabolism.

Because of the enormous therapeutic potential of tRes, there is a need for improved tRes analogs with increased bioavailability and longer half-lives. Such analogs or derivatives may have enhanced biological properties and, consequently, improved therapeutic efficacy. Similarly, there is a need for the identification of the molecular targets of tRes and its analogs because such information may lead to the design and development of improved therapeutic agents.

SUMMARY OF THE INVENTION

Briefly, therefore, the present invention provides a method for modulating activity of a cannabinoid receptor by contacting the cannabinoid receptor with a monomer or an oligomer of a compound comprising Formula (I) such that the activity of the cannabinoid receptor is modulated. The compound comprising Formula (I) has the following structure:

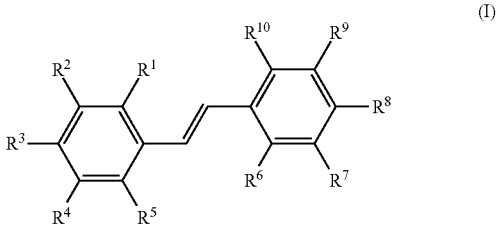

wherein:
$R^1$, $R^2$, $R^3$, $R^4$, $R^5$, $R^6$, $R^7$, $R^8$, $R^9$, and $R^{10}$ are independently chosen from hydrogen, hydroxyl, hydrocarbyl, substituted hydrocarbyl, hydrocarbyloxy, substituted hydrocarbyloxy, and sulfoxy; provided that at least one of the R groups is a hydroxyl or substituted hydroxyl group; and provided that if the compound comprising Formula (I) is monomeric, then the compound comprising Formula (I) is other than resveratrol.

Another aspect of the invention encompasses a method for preventing damage by a reactive nitrogen species in a cell. The method comprises contacting the cell with a monomer or an oligomer of a compound comprising Formula (I) such that the reactive nitrogen species is scavenged by the compound comprising Formula (I) and the cell is protected from damage from the reactive nitrogen species. The compound comprising Formula (I) has the following structure:

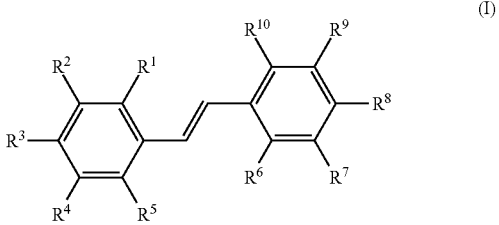

wherein:
$R^1$, $R^2$, $R^3$, $R^4$, $R^5$, $R^6$, $R^7$, $R^8$, $R^9$, and $R^{10}$ are independently chosen from hydrogen, hydroxyl, hydrocarbyl, substituted hydrocarbyl, hydrocarbyloxy, substituted hydrocarbyloxy, and sulfoxy; provided that at least one of the R groups is a hydroxyl or substituted hydroxyl group; and provided that if the compound comprising Formula (I) is monomeric, then the compound comprising Formula (I) is other than resveratrol.

Still another aspect of the present invention provides a compound comprising Formula (II):

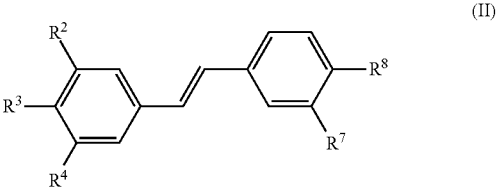

wherein:
$R^2$, $R^4$, and $R^8$ are independently chosen from hydroxyl, alkoxy, glucuronidyloxy, glucosyloxy, and sulfoxy;

R³ is alkenyl; and
R⁷ is chosen from hydrogen, hydroxyl, alkoxy, glucuronidyloxy, glucosyloxy, and sulfoxy.

Yet another aspect of the invention encompasses a pharmaceutical composition comprising a compound comprising Formula (II) and at least one pharmaceutically acceptable excipient. The compound comprising Formula (II) has the following structure:

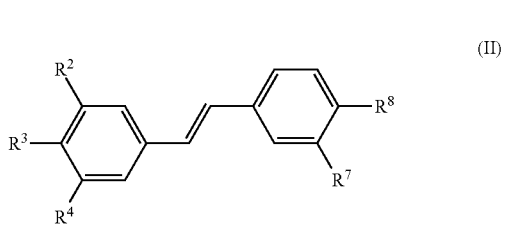

(II)

wherein:
$R^2$, $R^4$, and $R^8$ are independently chosen from hydroxyl, alkoxy, glucuronidyloxy, glucosyloxy, and sulfoxy;
$R^3$ is alkenyl; and
$R^7$ is chosen from hydrogen, hydroxyl, alkoxy, glucuronidyloxy, glucosyloxy, and sulfoxy.

Other features and iterations of the invention are described in more detail below.

DETAILED DESCRIPTION OF THE INVENTION

Figure 1:
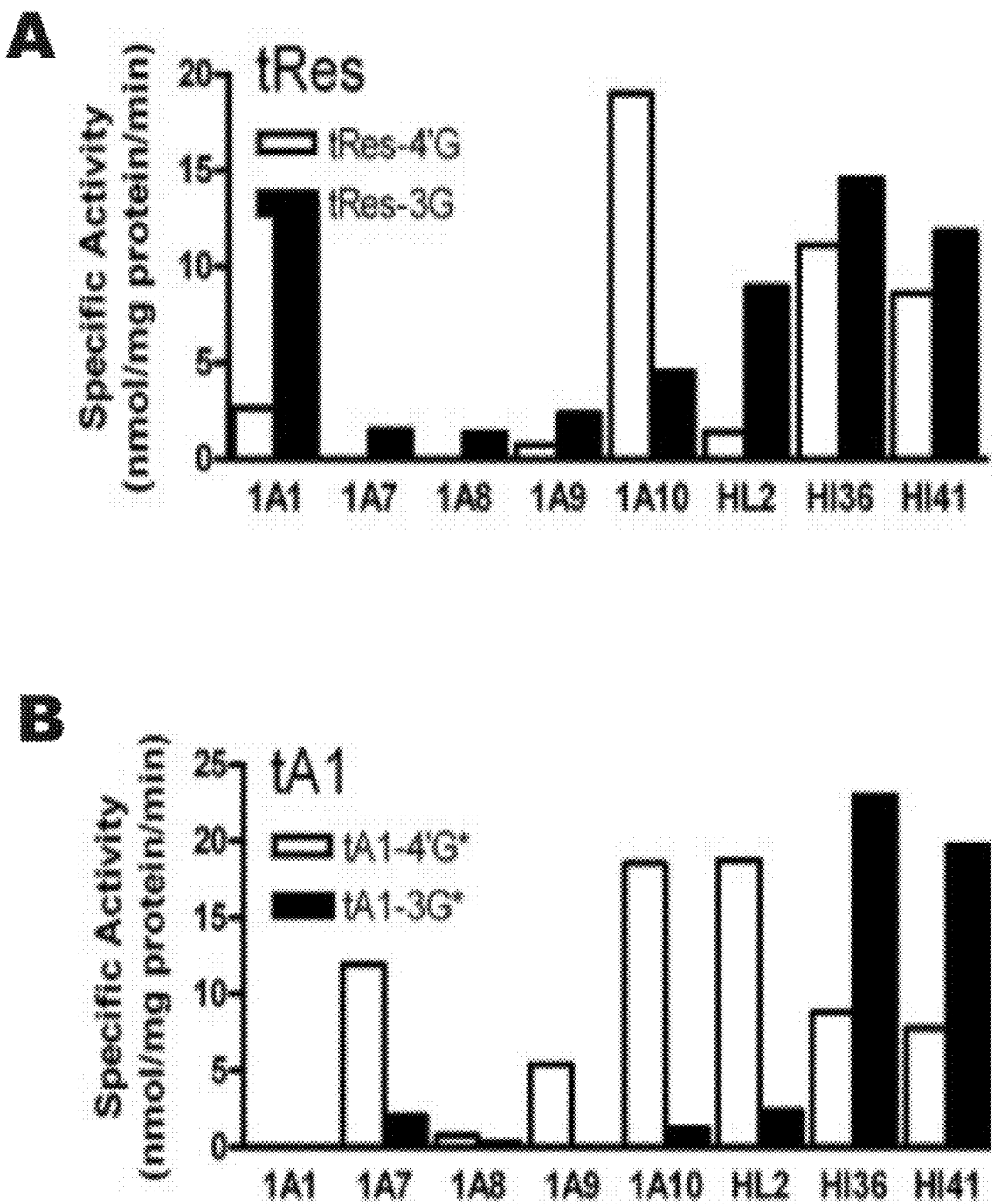
FIG. 1 illustrates the ability of human recombinant UGT1A isoforms (1A1, 1A7, 1A8, 1A9, 1A10), human liver microsomes (HL2), and human intestinal microsomes (HI36, HI41) to glucuronidate (A) trans-resveratrol (tRes), (B) trans-arachidin-1 (tA1), (C) trans-piceatannol (tPice), and (D) trans-arachidin-3 (tA3). Plotted is the specific activity of each isoform or enzyme preparation for 4'-glucuronidates (open bars) and 3'-glucuronidates (solid bars). * Postulated assignments based on HPLC elution order.
Figure 1:
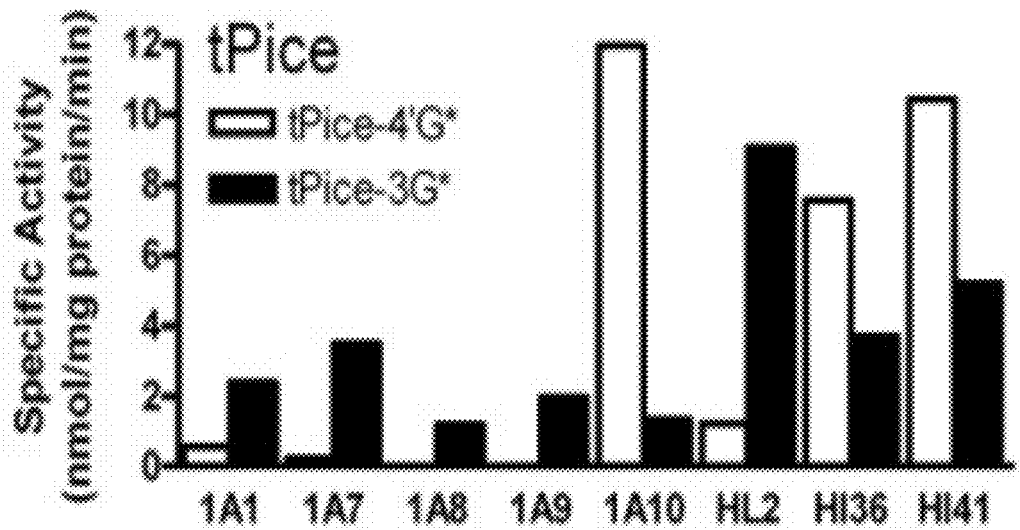
Figure 1:
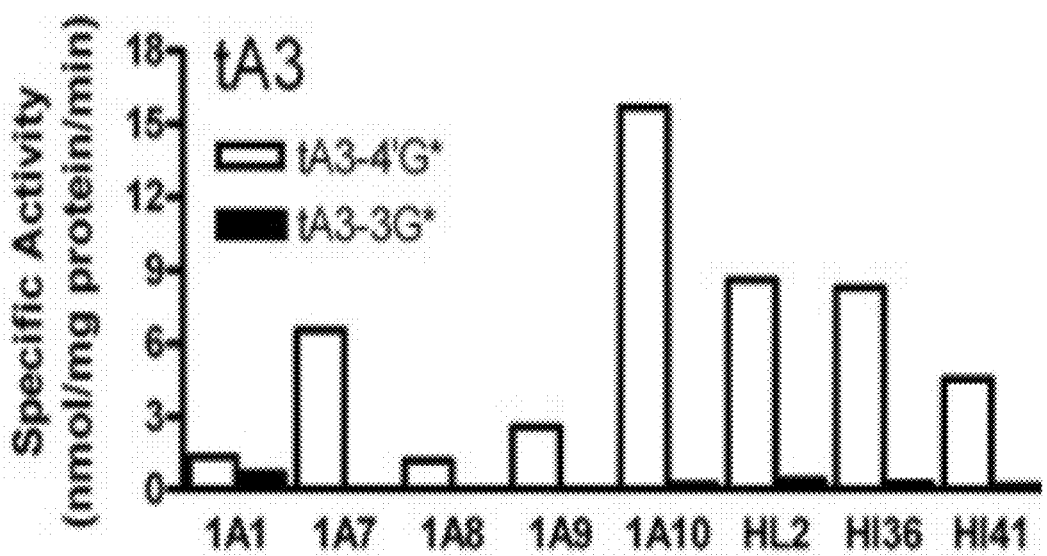
Figure 2A:
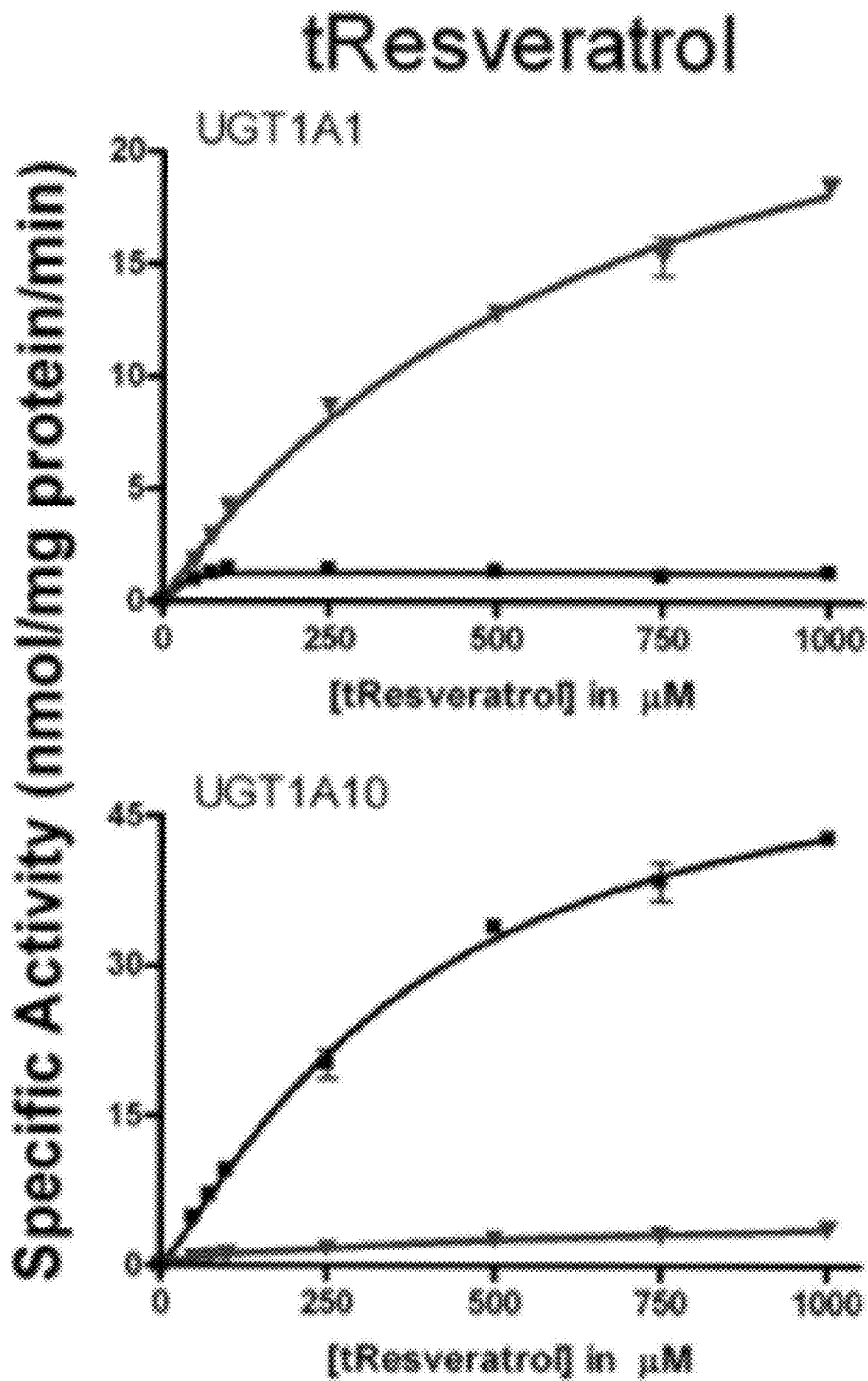
FIG. 2 depicts the kinetic analysis of glucuronidation. (A) trans-resveratrol, (B) trans-piceatannol, (C) trans-arachidin-1, and (D) trans-arachidin-3. Plotted is the specific activity of human UGT1A1 (upper plots) and UGT1A10 (lower plots) as a function of substrate concentration.
Figure 2B:
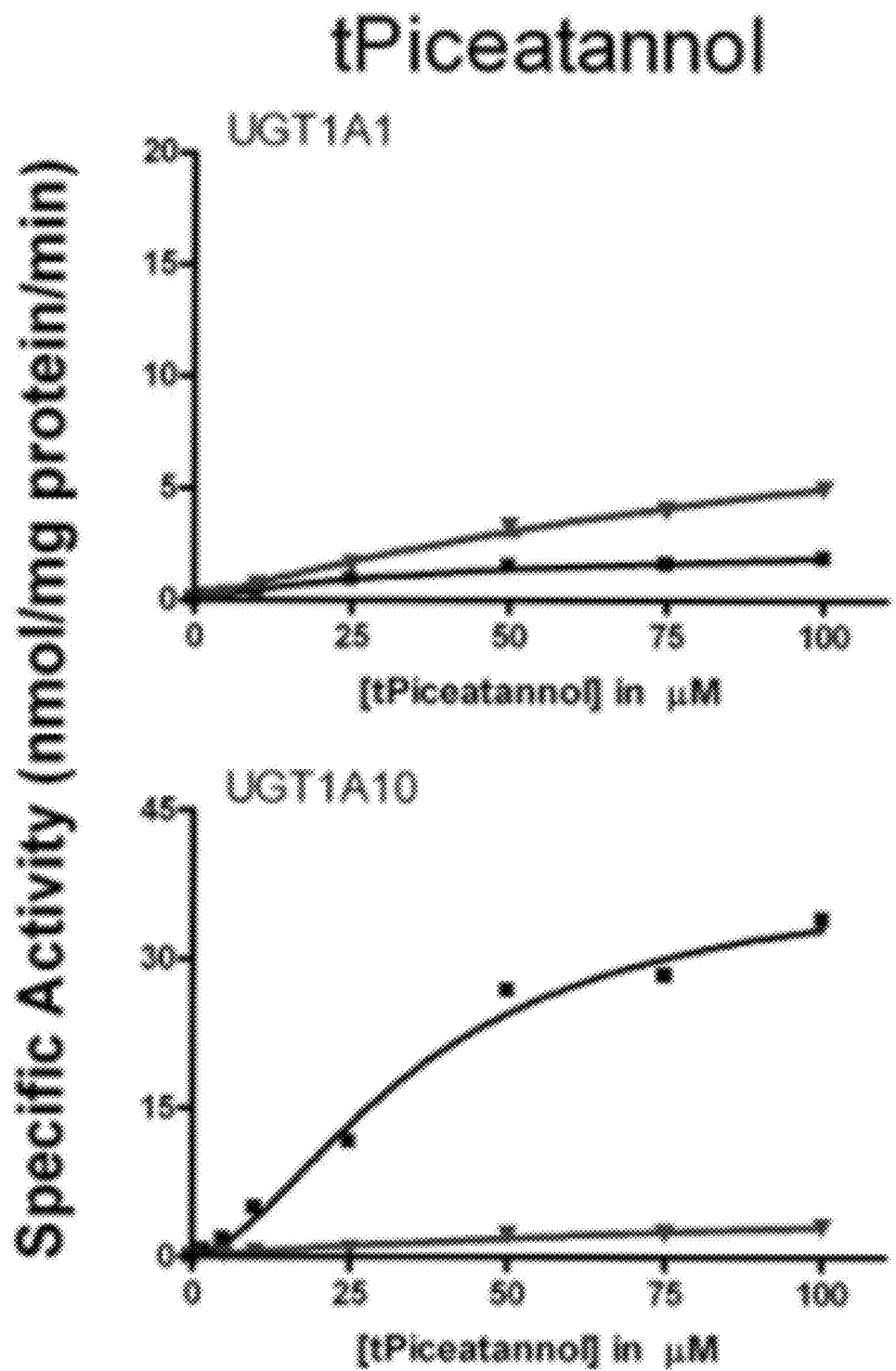
Figure 2C:
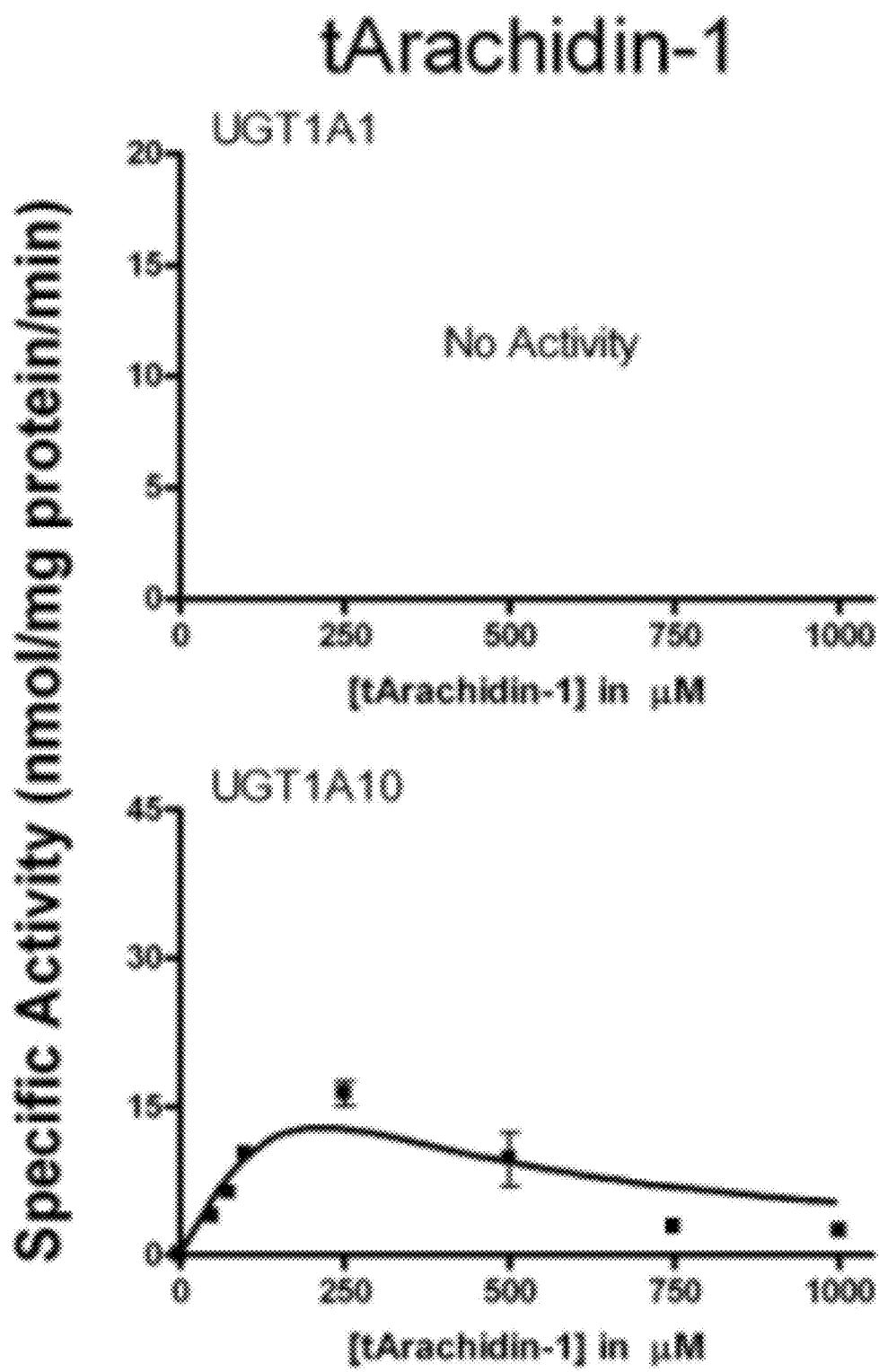
Figure 2D:
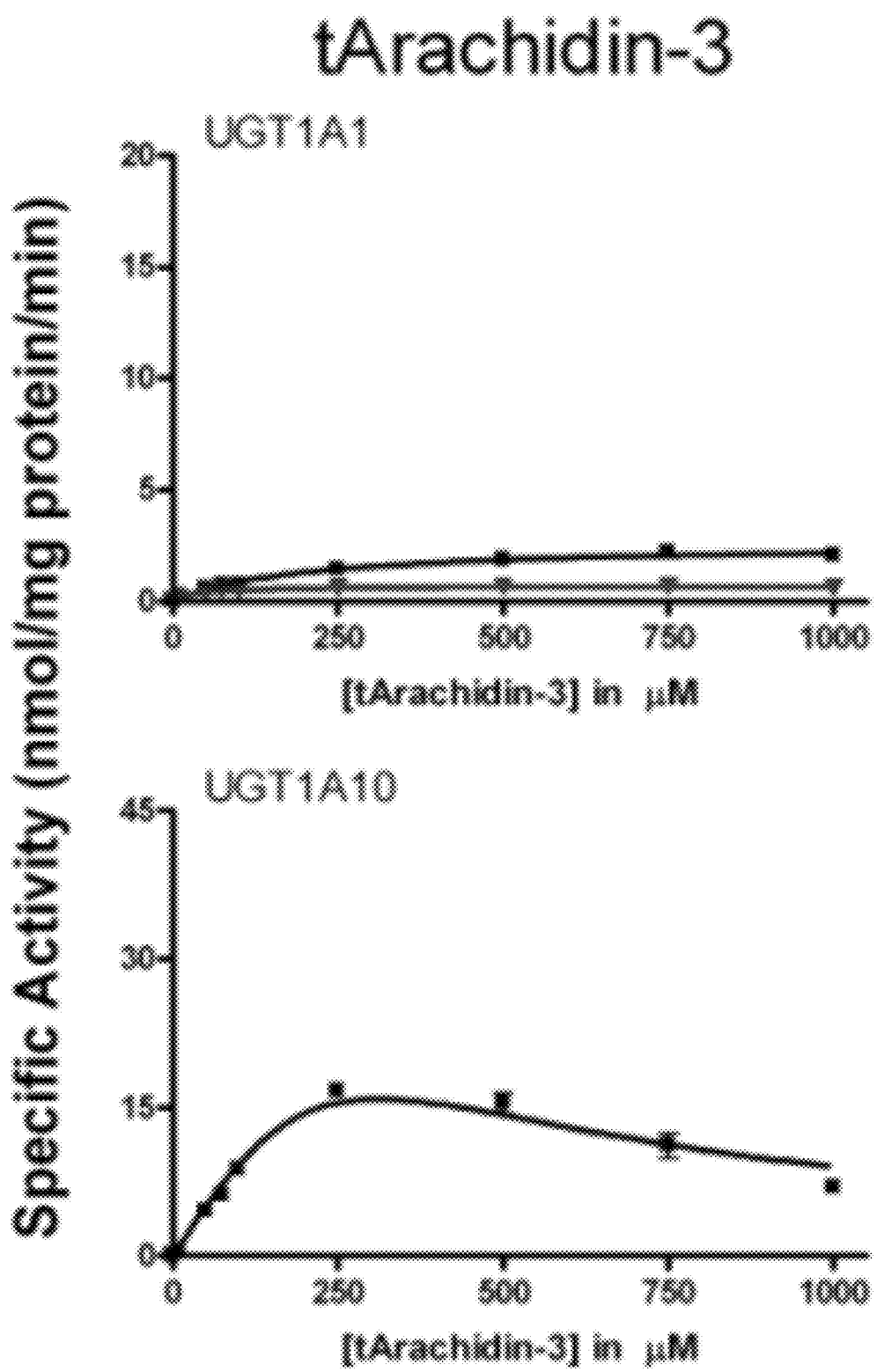

The present invention provides stilbenoid derivatives that have increased lipophilicity and/or increased negativity or hydrophilicity such that biological activity of the compound is altered relative to tRes. Accordingly, the stilbenoid derivatives may have increased in vivo bioavailability relative to tRes. Also provided herein is a method for using the stilbenoid derivatives to modulate the activity of cannabinoid receptors, wherein modulation of cannabinoid receptor activity may be used to treat a variety to medical conditions. The present invention also provides a method for preventing cellular damage by a reactive nitrogen species, wherein the method comprises scavenging the reactive nitrogen species with a stilbenoid derivative.

(I) Stilbenoid Derivatives
(a) Compounds Comprising Formula (I)

One aspect of the present invention is the provision of stilbenoid derivatives. In general, a stilbenoid is a derivatized stilbene comprising at least one hydroxyl group. A derivatized stilbenoid, therefore, refers to a hydroxylated stilbene that is derivatized with at least one additional group. The stilbenoid derivative may be a monomer or an oligomer of a compound comprising Formula (I):

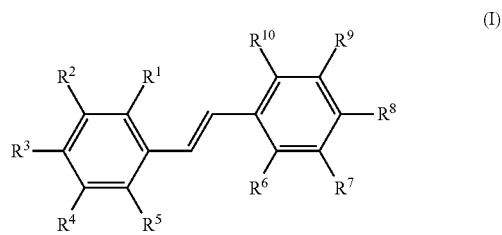

(I)

wherein:
$R^1$, $R^2$, $R^3$, $R^4$, $R^5$, $R^6$, $R^7$, $R^8$, $R^9$, and $R^{10}$ are independently chosen from hydrogen, hydroxyl, hydrocarbyl, substituted hydrocarbyl, hydrocarbyloxy, substituted hydrocarbyloxy, and sulfoxy; provided that at least one of the R groups is a hydroxyl or substituted hydroxyl group, and provided that if the compound comprising Formula (I) is monomeric, then the compound comprising Formula (I) is other than resveratrol.

In some embodiments, $R^1$, $R^2$, $R^3$, $R^4$, $R^5$, $R^6$, $R^7$, $R^8$, $R^9$, and $R^{10}$ are independently chosen from hydrogen, hydroxyl, alkyl, alkenyl, alkyoxy, alkenyloxy, aryloxy, glucuronidyloxy, glucosyloxy, and sulfoxy. Preferred alkenyl groups include isoprenyl (i.e., 3-methyl-1-butenyl), 3-methyl-but-2-enyl, and isopentadienyl. In further embodiments, $R^1$, $R^5$, $R^6$, $R^9$, and $R^{10}$ are hydrogen; $R^2$, $R^4$, $R^7$, and $R^8$ are chosen from hydrogen, hydroxyl, alkoxy, glucuronidyloxy, and sulfoxyl; and $R^3$ is chosen from hydrogen or alkenyl.

In one preferred embodiment, $R^1$, $R^3$, $R^5$, $R^6$, $R^7$, $R^9$, and $R^{10}$ are hydrogen; and $R^2$, $R^4$, and $R^8$ are independently chosen from hydroxyl, alkoxy, glucuronidyloxy, and sulfoxyl. In one iteration, for example, $R^2$, $R^4$, are methoxy and $R^8$ is hydroxyl. In another embodiment, $R^1$, $R^5$, $R^6$, $R^7$, $R^9$, and $R^{10}$ are hydrogen; $R^2$, $R^4$, and $R^8$ are independently chosen from hydroxyl, alkoxy, glucuronidyloxy, and sulfoxyl; and $R^3$ is alkenyl. In a further embodiment, $R^1$, $R^3$, $R^5$, $R^6$, $R^9$, and $R^{10}$ are hydrogen; $R^2$, $R^4$, and $R^8$ are independently chosen from hydroxyl, alkoxy, glucuronidyloxy, and sulfoxyl; and $R^7$ is alkenyl.

In still another embodiment, $R^1$, $R^3$, $R^5$, $R^6$, $R^9$, and $R^{10}$ are hydrogen; and $R^2$, $R^4$, $R^7$, and $R^8$ are independently chosen from hydroxyl, alkoxy, glucuronidyloxy, and sulfoxyl. In yet another embodiment, $R^1$, $R^5$, $R^6$, $R^9$, and $R^{10}$ are hydrogen; $R^2$, $R^4$, $R^7$, and $R^8$ are independently chosen from hydroxyl, alkoxy, glucuronidyloxy, and sulfoxyl; and $R^3$ is alkenyl.

In yet another embodiment, $R^1$, $R^3$, $R^5$, $R^6$, $R^7$, $R^8$, $R^9$, and $R^{10}$ are hydrogen; and $R^2$ and $R^4$ are independently chosen from hydroxyl, alkoxy, glucuronidyloxy, and sulfoxyl. In an alternate embodiment, $R^1$, $R^5$, $R^6$, $R^7$, $R^8$, $R^9$, and $R^{10}$ are hydrogen; $R^2$ and $R^4$ are independently chosen from hydroxyl, alkoxy, glucuronidyloxy, and sulfoxyl; and $R^3$ is alkenyl.

(b) compounds comprising Formula (II)

In preferred embodiments, the stilbenoid derivative may be a monomer or an oligomer of a compound comprising Formula (II):

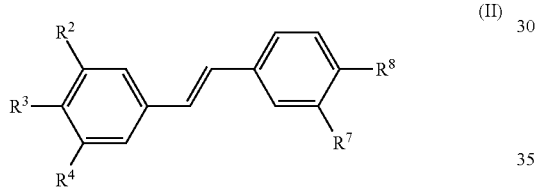

wherein:
  $R^2$, $R^4$, and $R^8$ are independently chosen from hydroxyl, alkoxy, glucuronidyloxy, and sulfoxy;
  $R^3$ is alkenyl; and
  $R^7$ is chosen from hydrogen, hydroxyl, alkoxy, glucuronidyloxy, and sulfoxy.

Preferably, $R^2$ and $R^8$ are independently chosen from hydroxyl, alkoxy, and sulfoxy; $R^3$ is alkenyl; $R^4$ is glucuronidyloxy, and $R^7$ is chosen from hydrogen, hydroxyl, alkoxy, and sulfoxy.

In one embodiment, the compound comprising Formula (II) comprises Formula (IIa):

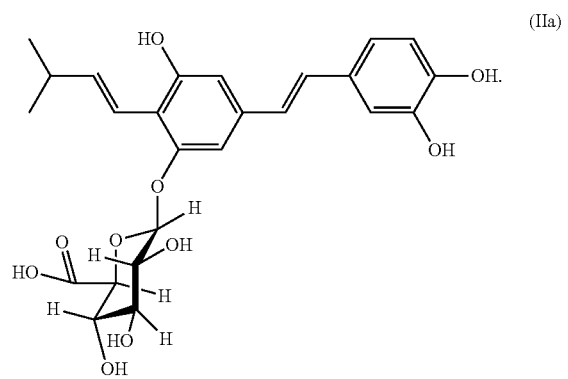

In another embodiment, the compound comprising Formula (II) comprises Formula (IIb):

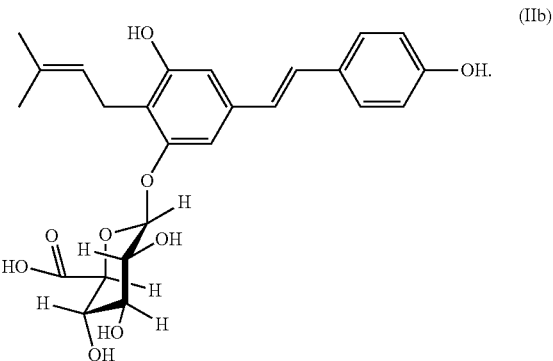

In a further embodiment, the compound comprising Formula (II) comprises Formula (IIc):

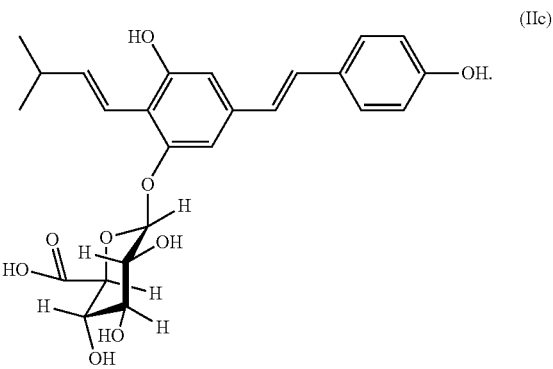

(c) Oligomers

Oligomers of any of the compounds described above in sections (I)(a) and (I)(b) may be dimers, trimers, tetramers, pentamers, hexamers, heptamers, and the like.

Those skilled in the art are familiar with the locations and linking groups that may link monomers of the compounds described above to form oligomers.

(d) Stereochemistry

Monomers of any of the compounds described above in sections (I)(a) and (I)(b) may be cis isomers or trans isomers. Preferentially, the monomers of the compounds detailed above are trans isomers.

Oligomers of any of the compounds described above in section (I)(c) may comprise cis isomers, trans isomers, or a combination of cis and trans isomers.

(e) Compositions Comprising a Compound Comprising Formula (II)

A further aspect of the invention encompasses a pharmaceutical composition comprising a compound comprising Formula (II), (IIa), (IIb), or (IIc) and at least one pharmaceutical excipient. Suitable compounds comprising Formula (II) are detailed above in section (I)(b).

(i) Excipients

Non-limiting examples of suitable excipients include diluents, binders, fillers, buffering agents, pH modifying agents, disintegrants, dispersing agents, stabilizers, preservatives, compaction agents, lubricants, coloring agents, and flavoring agents. The amount and types of excipients utilized to form the pharmaceutical composition may be selected according to known principles of pharmaceutical science.

In one embodiment, the excipient may include at least one diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lacitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may comprise a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

In another embodiment, the excipient may include a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may comprise a buffering agent. Representative examples of suitable buffering agents include, but are not limited to, MOPS, HEPES, TAPS, Bicine, Tricine, TES, PIPES, MES, Tris buffers or buffered saline salts (e.g., Tris buffered saline or phosphate buffered saline).

In various embodiments, the excipient may include a pH modifier. By way of non-limiting example, the pH modifying agent may be citric acid, sodium carbonate, or sodium bicarbonate.

In a further embodiment, the excipient may include a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Suitable effervescent disintegrants include sodium bicarbonate in combination with citric acid and sodium bicarbonate in combination with tartaric acid.

In another alternate embodiment, the excipient may also include a preservative. Non-limiting examples of suitable preservatives include antioxidants, such as alpha-tocopherol or ascorbate, and antimicrobials, such as parabens, chlorobutanol or phenol.

In yet another embodiment, the excipient may include a dispersion enhancer. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In a further embodiment, the excipient may include a lubricant. Non-limiting examples of suitable lubricants include minerals such as talc or silica; and fats such as vegetable stearin, magnesium stearate or stearic acid.

In still another embodiment, it may be desirable to provide a coloring agent. Suitable color additives include, but are not limited to, food, drug and cosmetic colors (FD&C), drug and cosmetic colors (D&C), or external drug and cosmetic colors (Ext. D&C).

In a further embodiment, the excipient may include flavoring agents. Flavoring agents may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oils (such as lemon oil, orange oil, grape and grapefruit oil), and fruit essences (such as apple, peach, pear, strawberry, raspberry, cherry, plum, pineapple, and apricot). In still another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; stevia-derived sweeteners; chloro derivatives of sucrose such as sucralose; sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof. In still another embodiment, the excipient may include a taste-masking agent. Taste-masking materials include cellulose hydroxypropyl ethers (HPC); low-substituted hydroxypropyl ethers (L-HPC); cellulose hydroxypropyl methyl ethers (HPMC); methylcellulose polymers and mixtures thereof; polyvinyl alcohol (PVA); hydroxyethylcelluloses; carboxymethylcelluloses and salts thereof; polyvinyl alcohol and polyethylene glycol co-polymers; monoglycerides or triglycerides; polyethylene glycols; acrylic polymers; mixtures of acrylic polymers with cellulose ethers; cellulose acetate phthalate; and combinations thereof.

The weight fraction of the excipient or combination of excipients in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

(ii) Exemplary Compositions

One exemplary composition comprises a compound comprising Formula (IIa) and at least one excipient. Another exemplary composition comprises a compound comprising Formula (IIb) and at least one excipient. A further exemplary composition comprises a compound comprising Formula (IIc) and at least one excipient.

(II) Methods for Preparing Stilbenoid Derivatives

The stilbenoid derivatives may be prepared by a variety of biological and/or chemical techniques. As detailed above in section (I), the stilbenoid or stilbenoid derivative may be monomeric or oligomeric. In some embodiments, stilbenoids, prenylated stilbenoids, and methoxylated stilbenoids may be produced using a hairy root culture system, such as that described in U.S. Pat. No. 7,666,677, the entire disclosure of which is incorporated herein by reference. For example, peanut hairy root cultures may be induced to produce stilbenoids and prenylated stilbenoids by contact with an elicitor such as sodium acetate, methyl jasmonate, or combinations thereof. The culture system may be a small reaction flask or it may be a large scale bioreactor. The stilbenoid may be purified from the culture medium and characterized using techniques known to persons skilled in the art.

In another embodiment, the stilbenoid may be isolated and purified from a plant that produces the stilbenoid or stilbenoid derivative of interest. In a further embodiment, the stilbenoid may be produced from microbial, plant, or animal cells engineered to express the enzymes involved in stilbenoid synthesis and/or derivatization. In yet another embodiment, the stilbenoid may be chemically synthesized from simpler precursor molecules.

The stilbenoid may be further derivatized using a variety of techniques. In some embodiments, the stilbenoid may be glucuronidated using a UDP-glucuronosyltransferase (UGT). Generally, the UGT will be a mammalian enzyme, and preferentially, a human liver UGT or human intestinal UGT. For example, the UGT may be within liver or intestinal cytosolic or microsomal preparations. Alternatively, the UGT may be purified from liver or intestinal cells. In other embodiments, the UGT may be a recombinant enzyme. The recombinant UGT may be expressed in a variety of cell types, including, for example, insect cells (such as Sf9 cells from *Spodoptera frugiperda* or S2 cells from *Drosophila melanogaster*), yeast cells (such as *Pichia, Saccharomyces*, or *Schizosaccharomyces*), microbial cells, animal cells, and the like. In an exemplary embodiment, a recombinant human UGT may be produced in baculovirus-infected Sf9 insect cells. The recombinant UGT may be purified from the cells and used in vitro. Alternatively, the recombinant UGT may be used in the expressing cells or in lysates of the expressing cells. Suitable human UGTs include UGT1A1, UGT1A3, UGT1A4, UGT1A5, UGT1A6, UGT1A7, UGT1A8, UGT1A9, UGT1A10, UGT2A1, UGT2A2, UGT2A3, UGT2B4, UGT2B7, UGT2B10, UGT2B11, UGT2B15, UGT2B17, UGT2B28, B3GAT1, B3GAT2, and B3GAT3.

In additional embodiments, the stilbenoid may undergo a sulfur transfer reaction catalyzed by a sulfotransferase (SULT). As detailed above for UGTS, the SULT may be a native liver or intestinal SULT enzymes or it may be a recombinant SULT enzyme. Suitable SULTs include SULT1A1, SULT1A2, SULT1A3, SULT1A4, SULT1B1, SULT1C2, SULT1C3, SULT1C4, SULT1D1P, SULT1E1, SULT2A1, SULT2B1, SULT4A1, and SULT6B1.

In still other embodiments, the stilbenoid may be contacted with suitable chemical reactants and optional catalysts to convert the stilbenoid into a derivatized stilbenoid. For example, the stilbenoid may be contacted with a methyl donor or a methylating agent such that a hydroxyl group is converted to a methoxy group. Similarly, the stilbenoid may be contacted with an alkyl donor or an alkylating agent to form a suitable derivative. Those of skill in the art will appreciate that a stilbenoid may undergo multiple derivatizations. For example, the stilbenoid may be prenylated and glucuronidated. In other case, the stilbenoid may be prenylated, glucuronidated, and sulfated. Alternatively, the stilbenoid may be prenylated and methylated.

(III) Method for Modulating Cannabinoid Receptor Activity

Another aspect of the invention encompasses a method for modulating activity of a cannabinoid receptor. The method comprises contacting the cannabinoid receptor with a monomer or oligomer of a compound comprising Formula (I), such that the activity of the cannabinoid receptor is modulated. Suitable examples of the compound comprising Formula (I) are detailed above in section (I)(a).

(a) Cannabinoid Receptor

Cannabinoid (CB) receptors are a class of G protein-coupled cell membrane receptors. Two subtypes of cannabinoid receptors, cannabinoid type 1 receptor (CB1) and cannabinoid type 2 receptor (CB2), have been characterized. The CB1 receptor is expressed mainly in the brain, but also in the lungs, liver and kidneys. The CB2 receptor is mainly expressed in the immune system and in hematopoietic cells. Evidence suggests that additional CB receptors may exist.

In an exemplary embodiment, the cannabinoid receptor may be a CB1 receptor. In another exemplary embodiment, the cannabinoid receptor may be a CB2 receptor. In yet another exemplary embodiment, the cannabinoid receptor may comprise both CB1 and CB2 receptors.

(i) In Vitro Cells

In some embodiments, the cannabinoid receptor may be within an isolated tissue, tissue homogenate, or fraction thereof. Suitable tissues that express endogenous cannabinoid receptors are listed above. In other embodiments, the cannabinoid receptor may be within an isolated cell or fraction thereof. Examples of cells that express endogenous cannabinoid receptors include neural cells, respiratory system cells, hepatic cells, renal cells, immune system cells (e.g., B cells, T cells, etc.), and hematopoietic cells.

Alternatively, the cell may express a recombinant cannabinoid receptor. Cells that may be engineered to express cannabinoid receptors include fungi or yeast, such as *Pichia, Saccharomyces*, or *Schizosaccharomyces*; insect cells, such as Sf9 cells from *Spodoptera frugiperda* or S2 cells from *Drosophila melanogaster*; and mammalian cell, such as mouse, rat, hamster, non-human primate, or human cells. When mammalian cell lines are used, the cell line may be any established cell line or a primary cell line that is not yet described. The cell line may be adherent or non-adherent, or the cell line may be grown under conditions that encourage adherent, non-adherent or organotypic growth using standard techniques known to individuals skilled in the art. Non-limiting examples of suitable mammalian cell lines include Chinese hamster ovary (CHO) cells, monkey kidney CVI line transformed by SV40 (COS7), human embryonic kidney line 293, baby hamster kidney cells (BHK), mouse sertoli cells (TM4), monkey kidney cells (CV1-76), African green monkey kidney cells (VERO), human cervical carcinoma cells (HeLa), canine kidney cells (MDCK), buffalo rat liver cells (BRL 3A), human lung cells (W138), human liver cells (Hep G2), mouse mammary tumor cells (MMT), rat hepatoma cells (HTC), HIH/3T3 cells, the human U2-OS osteosarcoma cell line, the human A549 cell line, the human K562 cell line, the human HEK293 cell lines, the human HEK293T cell line, and TR1 cells. For an extensive list of mammalian cell lines, those of ordinary skill in the art may refer to the American Type Culture Collection catalog (ATCC®, Mamassas, Va.). In an exemplary embodiment, the cells engineered to express the cannabinoid receptor are CHO cells.

Cell fractions or extracts may be prepared from cells that naturally express cannabinoid receptors or from cells engineered to express recombinant cannabinoid receptors. Suitable cell extracts or fractions include cell lysates, membrane fractions, and microsomal fractions.

(ii) In Vivo Cells

In other embodiments, the cannabinoid receptor may be an endogenous cannabinoid receptor within a subject. Suitable subjects include, without limit, humans, as well as companion animals such as cats, dogs, rodents, and horses; research animals such as rabbits, sheep, pigs, dogs, primates, mice, rats and other rodents; agricultural animals such as cows, cattle, pigs, goats, sheep, horses, deer, chickens and other fowl; zoo animals; and primates such as chimpanzees, monkeys, and gorillas. In a preferred embodiment, the subject may be a human.

(b) Contacting the Cannabinoid Receptor

The method of the invention comprises contacting the cannabinoid receptor with a monomer or oligomer of a compound comprising Formula (I). In embodiments in which the cannabinoid receptor is in vitro, the cell or fraction thereof may be contacted with the compound comprising Formula (I) by incubating the cell or fraction thereof with the compound. Thus, the cell or fraction thereof may be contacted with a buffer or a culture medium containing the compound comprising Formula (I).

In embodiments in which cannabinoid receptor is in vivo, the compound comprising Formula (I) may be administered to the subject by a variety of routes. For example, a composition comprising the compound comprising Formula (I) may be administered orally (via a solid or liquid dosage form), parenterally (i.e., subcutaneously, intradermally, intravenously, intramuscularly, intracranially, or intraperitoneally), or topically (i.e., transdermally or transmucosally).

The amount of the compound comprising Formula (I) contacted with the cannabinoid receptor can and will vary depending upon the mode of contact, the chemical identity of the compound comprising Formula (I), and so forth. Those of skill in the art are familiar with methods for determining the appropriate amount.

(c) Modulation of Cannabinoid Receptor Activity

Contact with the compound comprising Formula (I) modulates the activity of the cannabinoid receptor. Without being bound to any particular theory, it is believed that the compound comprising Formula (I) has affinity for the cannabinoid receptor and binds to a binding site of the cannabinoid receptor. The affinity ($K_i$) of the compound comprising Formula (I) may be less than about 200 µM, less than about 50 µM, less than about 20 µM, less than about 5 µM, less than about 1 µM, less than about 0.1 µM, less than about 50 nM, less than about 10 nM, less than about 1 nM, or less than about 0.1 nM.

In some embodiments, the compound comprising Formula (I) may fully activate the cannabinoid receptor and, thus, function as an agonist. In other embodiments, the compound comprising Formula (I) may partially activate the cannabinoid receptor and, thus, function as a partial agonist. In additional embodiments, the compound comprising Formula (I) may inhibit the cannabinoid receptor and, thus, function as an inverse agonist. In further embodiments, the compound comprising Formula (I) may block the action of cannabinoid receptor agonists and, thus, function as an antagonist.

In various embodiments, the compound comprising Formula (I) may increase activity of the cannabinoid receptor by at least about 10%, 20%, 40%, 60%, 80%, 100%, 150%, 200%, 300%, 400%, 500%, or more than 1000%. In other embodiments, the compound comprising Formula (I) may decrease activity of the cannabinoid receptor by at least about 10%, 20%, 40%, 60%, 80%, 100%, 150%, 200%, 300%, 400%, 500%, or more than 1000%.

Modulation of cannabinoid receptors in vivo may be used to treat a variety of conditions. As used herein, the terms "treat" or "treating" refer to preventing or delaying the onset of the condition; inhibiting or alleviating the symptoms associated with the condition; or slowing, inhibiting, or reversing the progression of the condition. Non-limiting examples of suitable conditions include obesity, drug dependence, inflammation, pain, cardiovascular conditions, cancer, neurodegenerative disorders, and age-related disorders.

(IV) Method for Preventing Cell Damage by Reactive Nitrogen Species

Yet another aspect of the invention provides a method for preventing damage by a reactive nitrogen species in a cell. The method comprises comprising contacting the cell with a monomer or oligomer of a compound comprising Formula (I) such that the reactive nitrogen species is scavenged by the compound comprising Formula (I) and the cell is protected from damage from the reactive nitrogen species. Suitable examples of the compound comprising Formula (I) are detailed above in section (I)(a).

(a) Reactive Nitrogen Species

A variety of reactive nitrogen species may be scavenged by the compound comprising Formula (I). In one embodiment, the reactive nitrogen species may be peroxynitrite ($ONOO^-$). In another embodiment, the reactive nitrogen species may be nitric oxide (.NO). In still another embodiment, the reactive nitrogen species may be nitrogen dioxide ($NO_2$). In a further embodiment, the reactive nitrogen species may be dinitrogen trioxide ($N_2O_3$). In yet another embodiment, the cell may comprise a combination of reactive nitrogen species.

(b) Contacting the Cell with a Compound Comprising Formula (I)

In some embodiments, the cell may be an isolated cell. Non-limiting examples of suitable in vitro cells and means of contacting the cell with the compound comprising Formula (I) are presented above in sections (III)(a)(i) and (III)(b), respectively. In other embodiments, the cell may be in vivo, i.e., within a subject. Suitable subjects and means of contacting the cell with the compound comprising Formula (I) are detailed above in sections (III)(a)(ii) and (III)(b), respectively. Non-limiting examples of suitable in vivo cells include renal, hepatic, neural, cardiac, vasculature, blood, epithelial, endocrine, immune, respiratory, gastric, intestinal, urogenital, muscle, and bone cells. In a preferred embodiment, the cell may be a renal cell. In an exemplary embodiment, the cell may be a renal cell and contact with the compound comprising Formula (I) may protect the renal cells from sepsis-induced damage.

Upon contact of the cell with the compound comprising Formula (I), the compound may bind to or scavenge the reactive nitrogen species or combination thereof. Binding or scavenging of the reactive nitrogen species essentially sequesters the reactive nitrogen species such that the reactive nitrogen species is unable to react with (e.g., oxidize, nitrate, etc.), modify, or damage cellular proteins or other molecules.

Definitions

To facilitate understanding of the invention, the following terms are defined.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups having at least one carbon-carbon double bond that preferably contain from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups having at least one carbon-carbon triple bond that preferably contain from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroaryl" embraces unsaturated heterocyclyl radicals. Examples of unsaturated heterocyclyl radicals, also termed "heteroaryl" radicals include unsaturated 3 to 8 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 8-membered heteromonocyclic group containing an oxygen atom, for example, pyranyl, furyl, etc.; unsaturated 3 to 8-membered heteromonocyclic group containing a sulfur atom, for example, thienyl, etc.; unsaturated 3- to 8-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 8-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2, 5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like. The term also embraces radicals where heterocyclyl radicals are fused with aryl radicals or a non-aromatic cyclic system. Examples of such fused bicyclic radicals include benzofuran, benzothiophene, and the like.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "hydrocarbyl" as used herein describes organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The terms "substituted hydrocarbyl," "substituted alkyl," "substituted alkenyl," and "substituted aryl," as used herein refer to hydrocarbyl, alkyl, alkenyl, and aryl moieties, respectively, that are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples demonstrate preferred embodiments of the invention.

Example 1

Glucuronidation of Resveratrol Analogs

The following example was designed to examine the glucuronidation of trans-resveratrol (tRes), trans-arachidin-1 (tA1), trans-arachidin-3 (tA3), and trans-piceatannol (tPice). Eight human recombinant UGT1A isoforms (UGT1A1, 1A3, 1A4, 1A6, 1A7, 1A8, 1A9, and 1A10; 5 µg) expressed as His-tag proteins in baculovirus-infected Sf9 insect cells and human liver microsomes (from one donor; HL2; 50 µg) and human intestinal microsomes (from two donors; HI36 and HI41; 50 µg) were evaluated for their ability to glucuronidate these four compounds. The concentrations of the substrate and co-substrate (i.e., UDP-GlcUA) were 250 µM and 4 mM, respectively. Glucuronidation products were analyzed by HPLC and LCMS/MS.

As shown in FIG. 1, unique product profiles were seen for each enzyme source with the major isoforms involved in each being predominantly hepatic UGT1A1 and UGT1A9 and extrahepatic UGT1A7 and UGT1A10. The production of a large amount to tA1-3G* by HIM suggests another isoform, possibly from the UGT2B family, is involved in the metabolism of this compound. tRes was glucuronidated to 3-O— and 4'-O-Glucs by both hepatic UGT1A1 and extrahepatic UGT1A10. The presence of an additional 3'-OH group on the B ring (i.e., phenol ring) of tRes in tPice decreased the formation of the 3-O-Gluc by UGT1A1 however the 4'-O-Gluc is still efficiently produced by UGT1A10. The presence of a prenyl group on ring A (tA3) resulted in significant inhibition of 3-O-glucuronidation by UGT1A1 and UGT1A10. The addition of a prenyl group and a hydroxyl group (tA1) completely blocked formation of any Gluc by UGT1A1, as well as the formation of the 3-O-Gluc by UGT1A10.

Figure 3A:
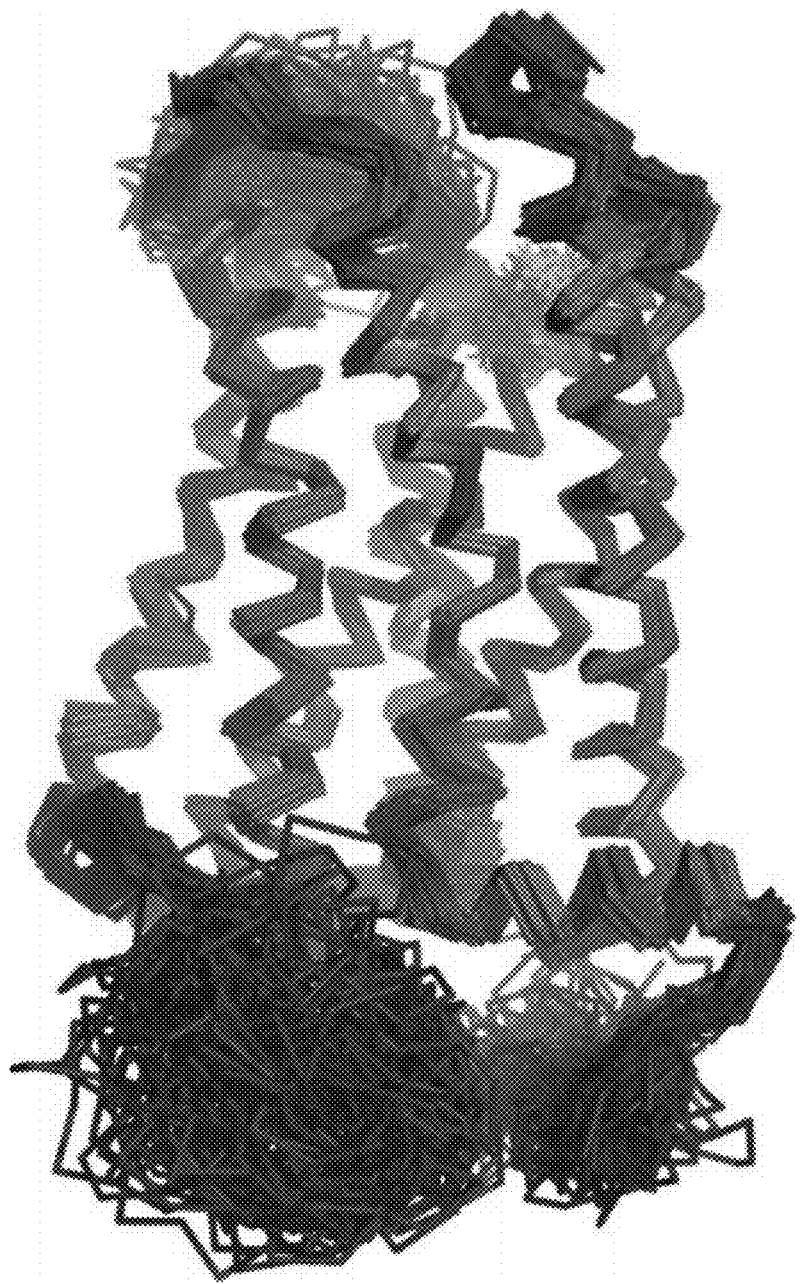
FIG. 3 illustrates molecular modeling of cannabinoid subtype 2 (CB2) receptor. (A) Conformational diversity observed in models generated using Modeller, represented by superposition of 132 CB2 structures. (B) Putative binding pose of tA2 bound to CB2 receptor model. (C) Putative binding pose of N-alkylisatinhydrazine (CB2 inverse agonist, $IC_{50}$: 131 nM) bound to CB2 receptor model.

The kinetic constants of the glucuronidation reactions using recombinant human UGT1A1 and UGT1A10 were determined by measuring the enzyme activity in the presence of increasing concentrations of substrate (see FIG. 2). The 4'-O-Gluc products of tA1 and 1A3 by UGT1A10 exhibited substrate inhibition kinetics. Table 1 presents the kinetic constants.

agonists involving docking several ligands on >100 models of CB2 receptors built using Modeller, based on a bovine rhodopsin X-ray structure. Since evidence has been reported of the particular importance of K109 and S285 for binding of CB2 ligands, S285 was selected as a central point for docking. The resulting models were found to have a considerable degree of difference in side-chain and backbone conformation (FIG. 3A).

From the docking results, poses were selected for which the common structure of docked ligands showed minimum root mean squared deviation (RMSD) and the predicted activities showed maximum correlation coefficients with experimentally estimated $pIC_{50}/pK_i$. After this initial selection followed by energy minimization, models that performed well in a small scale enrichment study, were tested and also

TABLE 1

Kinetic Constants

| Enzyme | Substrate | Product | Kinetics | $V_{max}$ (µM) | $K_m$ (nmol/mg protein/min) | $V_{max}/K_m$ | n (Hill coeff) |
|---|---|---|---|---|---|---|---|
| UGT1A1 | tRes | tRes-4'G | Hill | 1.3 ± 0.05 | 25.3 ± 4.8 | 0.44 | 2.2 |
|  |  | tRes-3G | M-M | 30.9 ± 2.0 | 705 ± 89 | 0.50 |  |
|  | tPice | tPice-4'G* | M-M | 2.8 ± 0.4 | 50.8 ± 16 | 0.54 |  |
|  |  | tPice-3G* | M-M | 13.5 ± 3.8 | 172 ± 67 | 0.78 |  |
|  | tA1 | tA1-4'G* | — | — | — | — |  |
|  |  | tA1-3G* | — | — | — | — |  |
|  | tA3 | tA3-4'G* | M-M | 2.6 ± 0.1 | 196 ± 24 | 0.01 |  |
|  |  | tA3-3G* | M-M | 0.67 ± 0.02 | 32.9 ± 5.2 | 0.02 |  |
| UGT1A10 | tRes | tRes-4'G | Hill | 55.8 ± 4.6 | 375 ± 62 | 0.14 | 1.2 |
|  |  | tRes-3G | M-M | 4.6 ± 0.3 | 347 ± 63 | 0.13 |  |
|  | tPice | tPice-4'G* | Hill | 38.9 ± 4.2 | 36.6 ± 6.1 |  | 1.7 |
|  |  | tPice-3G* | M-M | 7.0 ± 2.5 | 133 ± 72 | 0.05 |  |
|  | tA1 | tA1-4'G* | USI | ** | ** | ** |  |
|  |  | tA1-3G* | — | — | — | — |  |
|  | tA3 | tA3-4'G* | USI | ** | ** | ** |  |
|  |  | tA3-3G* | — | — | — | — |  |

— No activity
** Atypical kinetics profiles make it difficult to predict kinetic values.

Example 2

Molecular Modeling of Cannabinoid Receptor Binding

There have been limited efforts reported in the literature to predict the activity and selectivity of cannabinoid receptor antagonists and agonists. Most of the computational efforts for cannabinoids have used 3D-QSAR modeling (CoMFA and/or CoMSIA), which requires alignment of 3D-conformations for ligands. Because of this limitation, 3D-QSAR analyses, which generally are applied only to a set of compounds with common backbone and are not appropriate for simultaneous modeling of multiple classes of compounds, cannot be expected to be helpful for the prediction of the activity of novel classes of compounds.

To deal with the limitations of existing molecular models, therefore, activity and selectivity models for CB1 antagonists and CB2 agonists were prepared. These models are based on multiple chemical classes of reported CB receptor ligands, using support vector machines, and pharmacophore models, which summarize the arrangement of physicochemical functional groups needed for binding to CB1 and CB2.

Multiple models of CB2 were prepared using an extensively optimized protocol for docking and enrichment of CB2 found to perform efficiently in a large scale enrichment study, retrieving known CB2 ligands (14-85% of the training set CB2 ligands in the top 1% of predicted CB2 hits) from a huge pool of decoys (~229,000).

Figure 3B:
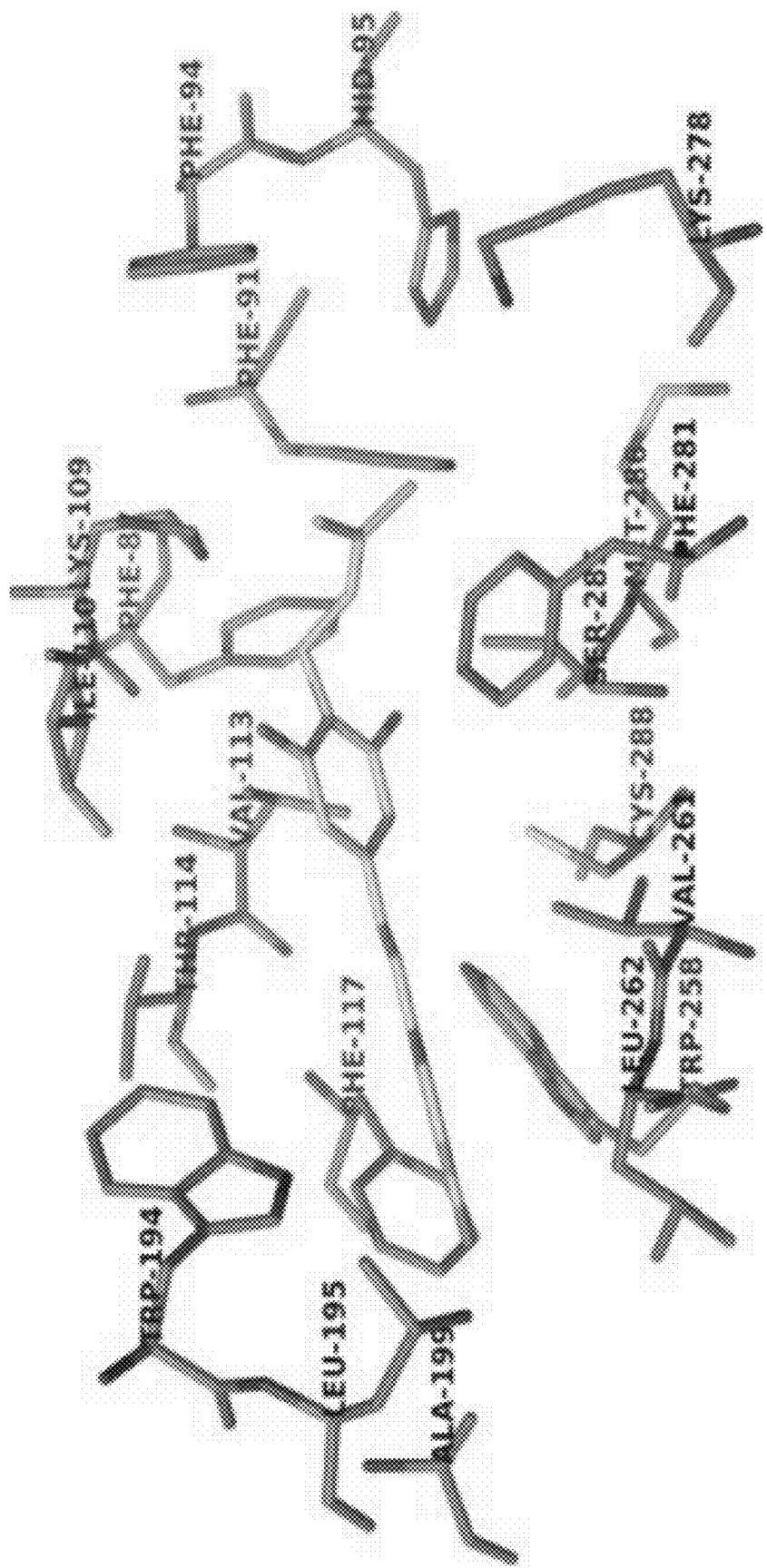
Figure 3C:
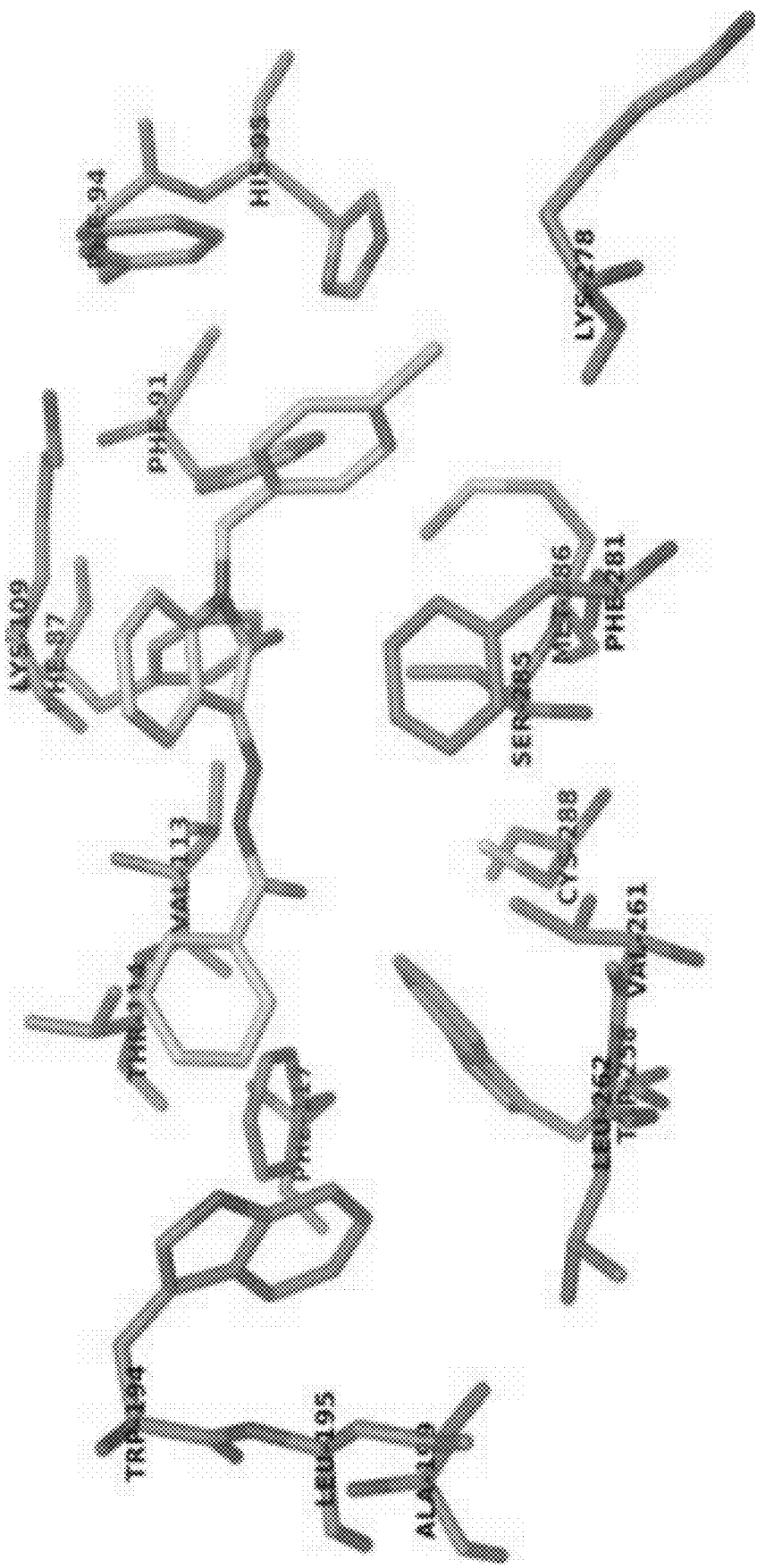

Basic docking of tRes-like ligands on 132 models of CB2 were performed. The selected best model, which showed low RMSD among the docked ligands and passed visual inspection, was used to rationalize observed difference in binding of 5 ligands (tRes, tPice, tA1, tA2, tA3). In the docked poses, these ligands interact with three regions of CB2, forming a hydrogen bond with S285 and hydrophobic interactions with two pockets, one formed by F87, F91, F281, K109, M286 and another formed by F117, W258, W194 and I198 (see FIG. 3B). The B ring (i.e., phenol ring) orients into the former hydrophobic pocket, while the A ring orients into the latter hydrophobic pocket. Either a 3-OH or 5-OH group forms a hydrogen bond with S285. The isoprenyl moiety of the arachidins improves the predicted binding, while increases in hydrophilicity of the phenol ring (additional OH groups), which interacts with a hydrophobic pocket, reduces the predicted binding. Table 2 presents Glide G scores (more negative corresponds to higher affinity) of the tRes analogs.

TABLE 2

Glide Scores and $K_i$ Values for CB2.

| Ligand | GScore | $K_i$ (μM) |
|---|---|---|
| 3-Gluc-tA3 | −7.51 | — |
| tA2 | −7.48 | — |
| tA3 | −7.11 | 11.3 ± 0.6 |
| 3-Gluc-tA2 | −7.00 | — |
| tA1 | −6.95 | 12.6 ± 1.7 |
| 3-Gluc-tA1 | −6.88 | — |
| tRes | −6.66 | 65.5 ± 12 |
| tPice | −6.27 | 114 ± 7.8 |
| 4'-Gluc-tPice | −6.03 | — |
| 3-Gluc-tRes | −5.95 | — |
| 3-Gluc-tPice | −5.86 | >100 |
| 4'-Gluc-rRes | −5.71 | >100 |

Example 3

Cannabinoid Receptor Binding Studies

Figure 4:
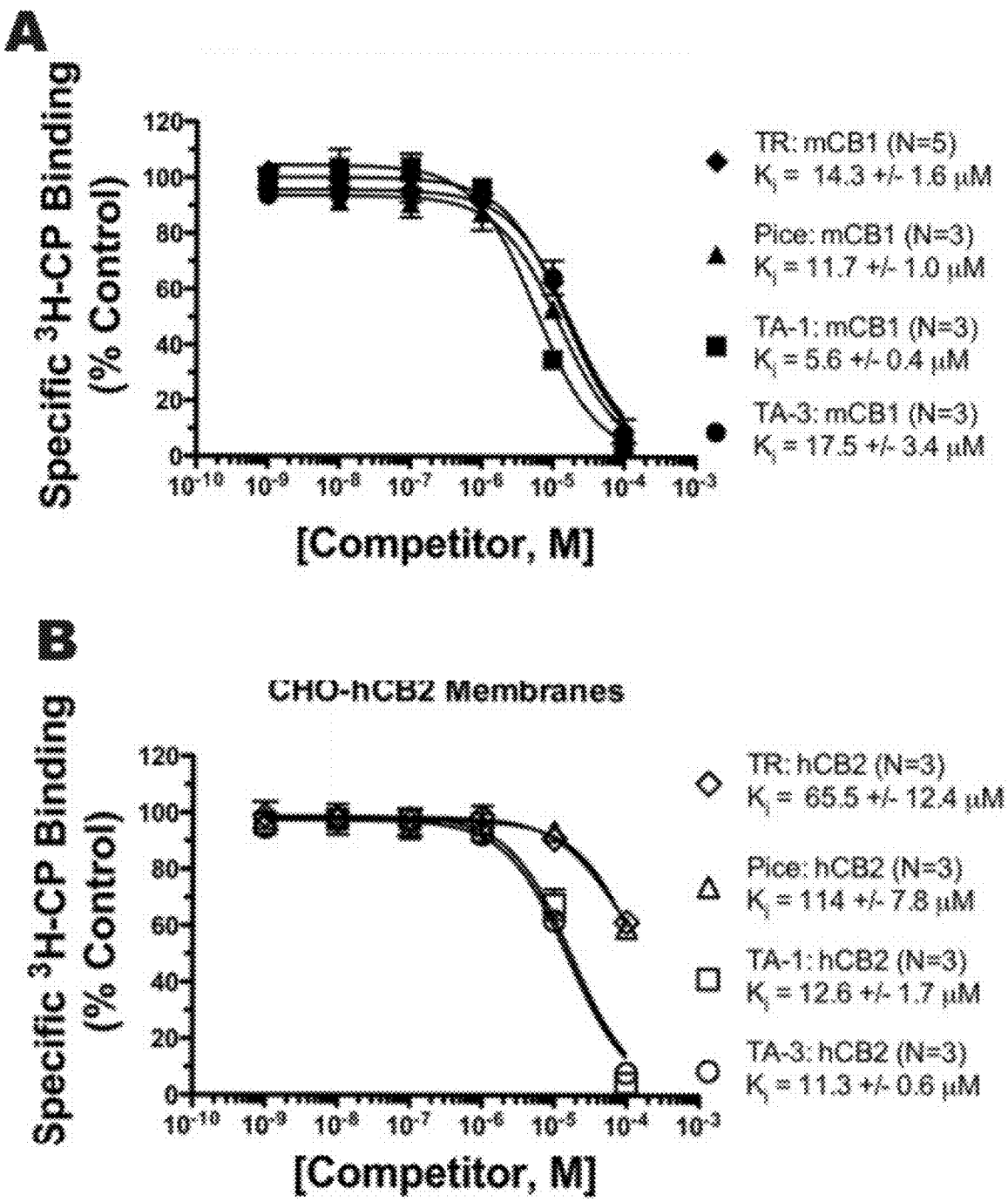
FIG. 4 presents binding curves and affinities of tRes and analogs for cannabinoid receptors. Plotted is the percent of control $^3$H-CB binding in the presence of increasing concentrations of tRes (TR), tPice (Pice), tA1 (TA-1), and tA3 (TA-3) in mouse brain-mCB1 membranes (A) and CHO-hCB2 membranes (B).

To determine the binding affinity of tRes and its analogs to CB receptors, in vitro binding studies were performed. Membrane preparations were prepared from mouse brain to examine CB1 binding. For CB2 binding, membrane preparations were prepared from CHO cells stably transformed with human CB2. Membranes were incubated with 0.2 nM $^3$H—CP (i.e., CP 55,940, a CB1 agonist) and increasing concentrations of tRes, tPice, tA1, or tA3 for 90 min at room temperature, and then filtered.

tRes and all analogs bound to CB1 receptors with affinities ($K_i$) in the low 5-20 μM range (FIG. 4, upper). The rank order for CB1 was tA1>tPice>tRes=tA3. Although tA1 and tA3 also bound to CB2 with similar affinities as CB1 (FIG. 4, lower), tRes and tPice had 6- to 10-fold lower affinities for CB2 than that observed for CB1.

In addition, all compounds except for tA3 exhibited approximately 2- to 10-fold selectively for binding to CB1 relative to CB2. Based on these observations, it appears that addition of the isoprenyl group, found only in tA1 and tA3, significantly enhances the binding affinity of these analogs for CB2 by approximately 6-10-fold. Furthermore, combination of the isoprenyl group and an additional hydroxyl group in tA1 apparently also modestly enhanced the binding affinity of this analog for CB1 by 2-fold. In summary, these studies clearly establish that tRes and several structurally related analogs bind to both CB1 and CB2 receptors with a low μM affinity. Most importantly, observations that minor modifications to the basic tRes structure resulted in marked alterations in the affinity of various analogs for CB receptors, indicate that tRes likely represents a useful scaffold for future design of selective and efficacious CB1 and CB2 ligands.

Table 2, above, also presents the $K_i$ values for CB2. There is an excellent correlation between the predicted values (G-scores) and the observed $K_i$ values.

Example 4

Reactive Nitrogen Species Scavenging

Reactive nitrogen species (NRS) play important roles in many of the diseases and conditions reported to be ameliorated by tRes. To examine this in more detail, a RNS scavenging assay was developed. The assay uses nitration of bovine serum albumin (BSA) and oxidation of glutathione (GSH) to monitor two biologically relevant toxic consequences of ONOO$^-$ production: protein nitration and thiol oxidation. Accordingly, BSA was incubated with authentic ONOO$^-$ in the presence of varying concentrations of tRes. The scavenging activity of tRes was compared to that of N-acetylcysteine (NAC).

Figure 5:
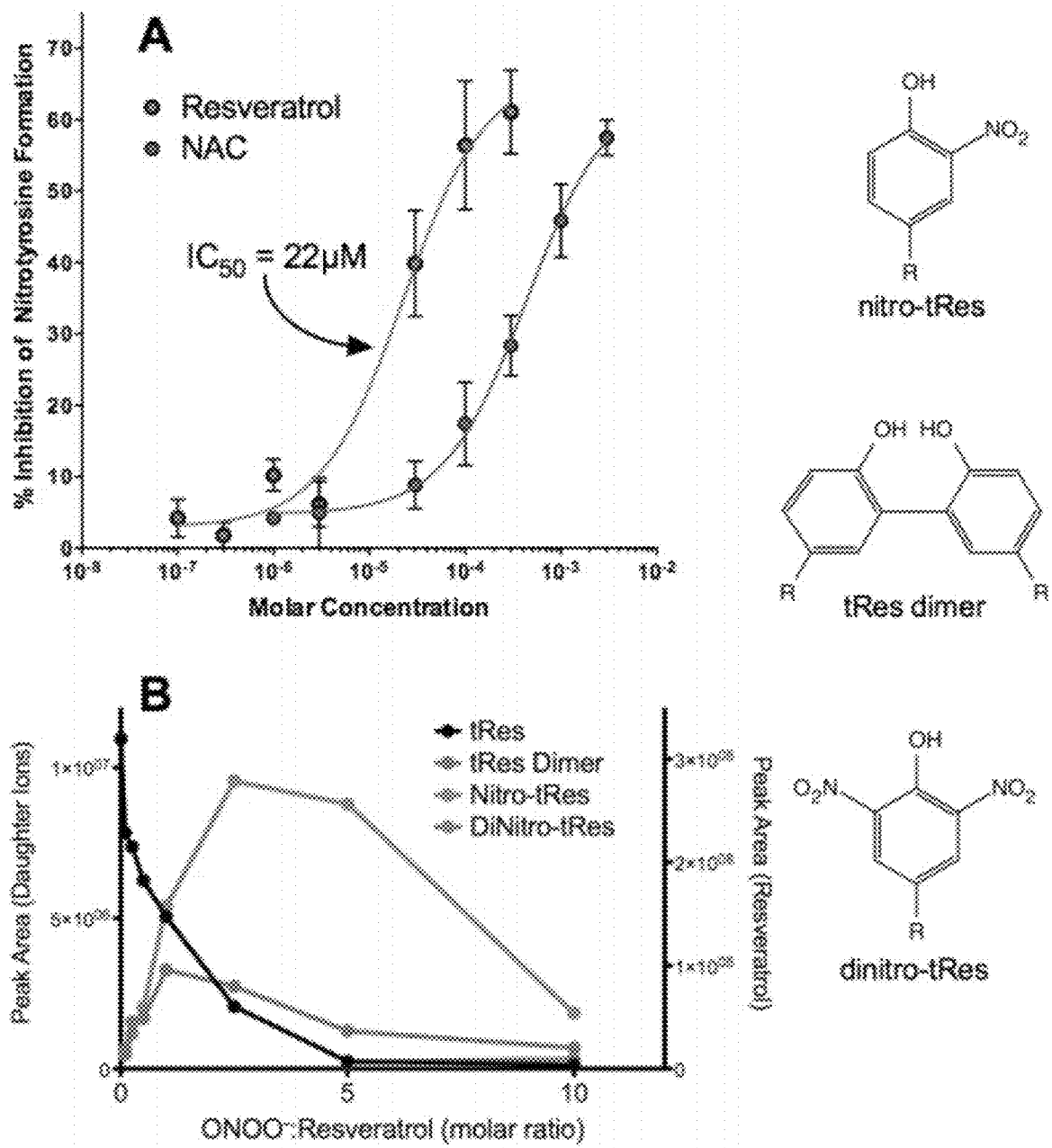
FIG. 5 depicts reactive nitrogen species (RNS) scavenging activity of tRes. (A) Plotted is the percent inhibition of protein nitration by tRes and N-acetylcysteine (NAC). (B) LC/MS/MS analysis of daughter ions identified nitro and tRes dimmers produced as tRes was consumed. Dinitro-tRes appeared at higher ONOO⁻:tRes ratios.

It was found that tRes inhibited nitration with an IC$_{50}$ of about 22 μM (see FIG. 5A). tRes was about 20-fold more potent than the known ONOO$^-$ scavenger NAC. Moreover, reacting tRes with authentic ONOO$^-$ or the ONOO$^-$ generator SIN-1 resulted in nitrated tRes and tRes dimers identified by LC/MS/MS (see FIG. 5B).

Example 5

Effect of tRes on Murine Model of Sepsis

Figure 6:
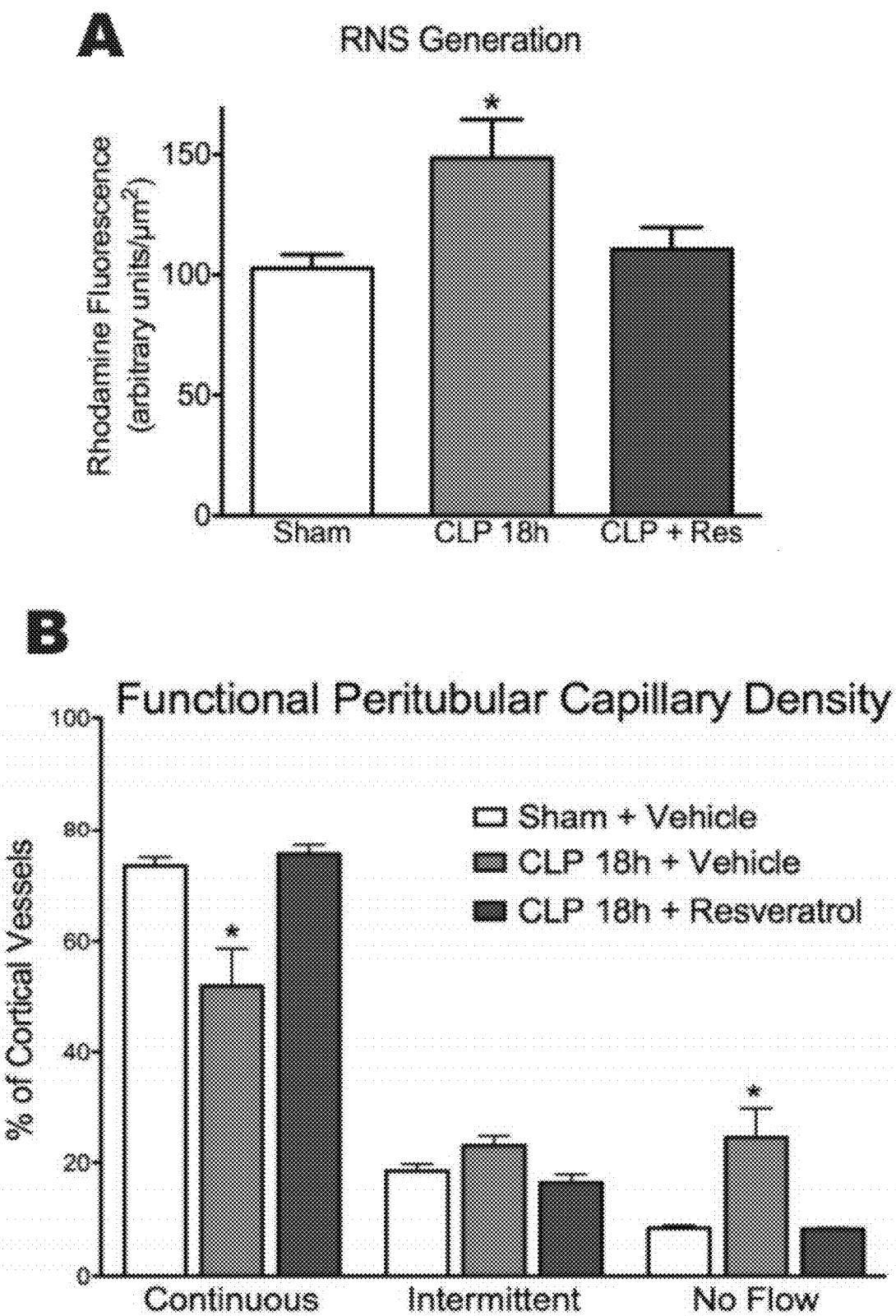
FIG. 6 shows the effect of tRes on a murine model of sepsis. (A) presents RNS generation in each treatment group. (B) presents the functional peritubular capillary density in each group. * P<0.05 compared to sham.

An established murine cecal ligation and puncture model (CLP) of sepsis-induced renal injury (Wu et al., J. Am. Soc. Nephrol., 2007, 18:1807-1815) was used to assess potency and efficacy of tRes. tRes (30 mg/kg) was administered by i.p. 30 min prior to and 6 hr post CLP. Control (sham) mice underwent surgery but not CLP. Each treatment group contained 4-5 mice. Renal ONOO$^-$ generation (rhodamine fluorescence) and renal peritubular capillary perfusion were quantified using intravital video microscopy (IVVM) on anesthetized mice in each of the treatment groups. At 18 hr post CLP, tRes blocked RNS generation in the kidney and preserved renal capillary perfusion (see FIG. 6).

Example 6

Inhibition of G-Protein Activity

Figure 7:
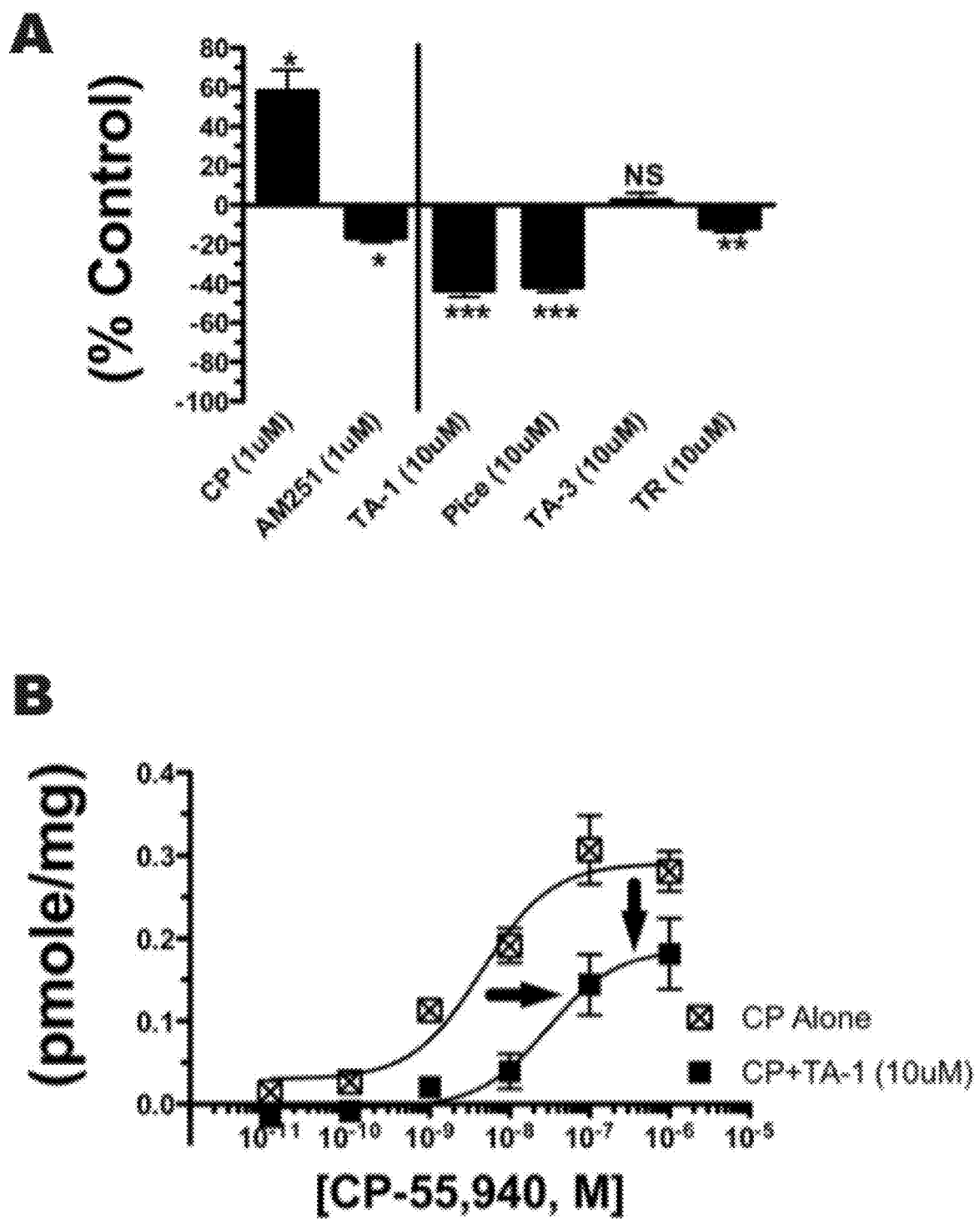
FIG. 7 presents the intrinsic activity of tRes and analogs at CB1 receptors. (A) presents the percent of control G-protein activity in the presence of the indicated compounds. (B) plots $^{35}$S-GTPγS binding in the presence of tA1 and increasing concentration of the CB1 agonist CP-55,940. (C) presents $^{35}$S-GTPγS binding in the presence of tA3 and increasing concentration of CP-55,940. *, **=significantly different (P<0.05, 0.01) from 0%. NS=not significantly different from 0%.

Studies were initiated to determine the intrinsic activity of tRes and its analogs at CB1 receptors by measuring the activity of CB1 receptor-stimulated G-protein activity. For this, mouse brain membranes were incubated with 0.1 nM $^{35}$S-GYPγS and either 1 μM CP-55,940 (CB1 agonist), 1 μM AM251 (CB1 inverse agonist), or 10 μM of tRes (TR), tPice, tA1, or tA3 for 30 min at 30° C., and then filtered As expected CP-55,940 stimulated and AM251 inhibited G-protein activity in mouse brains expressing CB1 receptors (FIG. 7A). Both stimulation and inhibition were blocked by co-incubation with the selective CB1 neutral antagonist O-2050 (data not shown). It was found, however, that 10 μM of tA-1 and Pice markedly reduced basal G-protein activity, while 10 μM of tA-3 and tRes had little effect on basal G-protein activity. Although it has not been determined whether the potential inverse activity produced by tA-1 and Pice could be mediated by CB1 receptors, clearly none of the tested analogs acted as agonists at CB1 receptors to stimulate G-proteins.

Figure 7C:
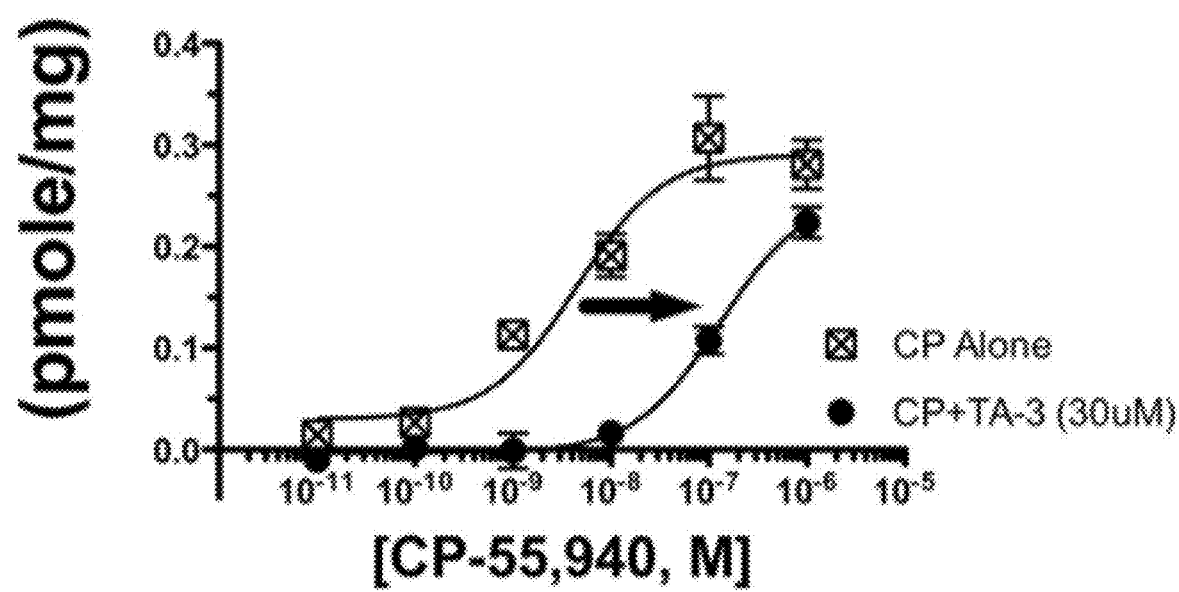

To examine the possible antagonist activity of these compounds, G-protein activity was measured in the presence of tA1 or tA3 and increasing concentrations of the CB1R agonist CP-55,940. It was found that incubation with 10 μM tA-1 or 30 μM of tA-3 appeared to result in CB1R antagonism, producing a 7-fold (4.3 vs 28 nM) or 30-fold (4.3 vs 127 nM) increase (shift-to-the-right) in the ED$_{50}$ required to activate G-proteins by CP-55,940, respectively (FIGS. 7B and 7C). Moreover, in addition to increasing the ED$_{50}$, tA-1 but not tA-3 also significantly reduced the maximal response produced by CP-55,940 from 0.34+/−0.03 to 0.22+/−0.04 pmole/mg protein. This indicates that tA-1 may produce CB1 receptor antagonism by both competitive and non-competitive mechanisms.

What is claimed is:

1. A method for inhibiting damage by a reactive nitrogen species, the method comprising administering a monomer or an oligomer of a compound of Formula (I) to a subject in need thereof such that the reactive nitrogen species is scavenged by the compound of Formula (I) and damage by the reactive nitrogen species is inhibited, the compound of Formula (I):

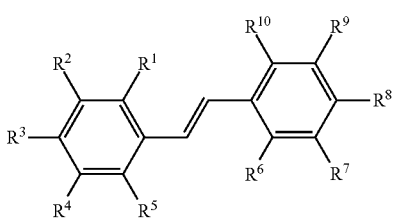

(I)

wherein:

$R^1$, $R^2$, $R^3$, $R^4$, $R^5$, $R^6$, $R^7$, $R^8$, $R^9$, and $R^{10}$ are independently hydrogen, hydroxyl, hydrocarbyl, substituted hydrocarbyl, hydrocarbyloxy, substituted hydrocarbyloxy, or sulfoxy; provided that at least one of the R groups is a hydroxyl or substituted hydroxyl group; and provided that if the compound of Formula (I) is monomeric, then it is other than a compound in which (i) $R^1$, $R^3$, $R^5$, $R^6$, $R^7$, $R^9$, and $R^{10}$ are hydrogen, and $R^2$, $R^4$, and $R^8$ are hydroxyl; or (ii) $R^1$, $R^3$, $R^5$, $R^6$, and $R^{10}$ are hydrogen, $R^2$, $R^4$, $R^7$, and $R^9$ are hydroxyl, and $R^8$ is methoxy.

2. The method of claim 1, wherein $R^1$, $R^2$, $R^3$, $R^4$, $R^5$, $R^6$, $R^7$, $R^8$, $R^9$, and $R^{10}$ are independently hydrogen, hydroxyl, alkyl, alkenyl, alkyoxy, alkenyloxy, aryloxy, glucuronidyloxy, glucosyloxy, or sulfoxy.

3. The method of claim 1, wherein $R^1$, $R^5$, $R^6$, $R^7$, $R^9$, and $R^{10}$ are hydrogen; $R^3$ is alkenyl; and $R^2$, $R^4$, and $R^8$ are independently hydroxyl, alkoxy, glucuronidyloxy, or sulfoxy.

4. The method of claim 1, wherein $R^1$, $R^5$, $R^6$, $R^9$, and $R^{10}$ are hydrogen; $R^3$ is hydroxyl or alkenyl; and $R^2$, $R^4$, $R^7$, and $R^8$ are independently hydroxyl, alkoxy, glucuronidyloxy, or sulfoxy.

5. The method of claim 1, wherein the compound of Formula (I) is a cis isomer or a trans isomer.

6. The method of claim 1, wherein the oligomer of the compound of Formula (I) comprises cis isomers, trans isomers, or a combination of cis and trans isomers.

7. The method of claim 1, wherein the reactive nitrogen species is peroxynitrite, nitric oxide, nitrogen dioxide, or dinitrogen trioxide.

8. The method of claim 1, wherein the subject is a rodent, a research animal, a companion animal, an agricultural animal, or a human.

9. The method of claim 1, wherein $R^1$, $R^5$, $R^6$, $R^9$, and $R^{10}$ are hydrogen; $R^2$, $R^4$, and $R^8$ are independently hydroxyl, alkoxy, glucuronidyloxy, or sulfoxy; $R^3$ is isoprenyl; and $R^7$ is hydrogen, hydroxyl, alkoxy, glucuronidyloxy, or sulfoxy.

10. The method of claim 9, wherein $R^2$, $R^4$, $R^7$, and $R^8$ are hydroxyl; and $R^3$ is 3-methyl-1-butenyl.

11. The method of claim 9, wherein $R^2$, $R^4$, and $R^8$ are hydroxyl; $R^7$ is hydrogen; and $R^3$ is 3-methyl-but-2-enyl.

12. The method of claim 1, wherein $R^2$, $R^4$, and $R^8$ are hydroxyl; $R^7$ is hydrogen; and $R^3$ is 3-methyl-1-butenyl.

* * * * *